United States Patent [19]
Arita et al.

[11] Patent Number: 5,612,190
[45] Date of Patent: Mar. 18, 1997

[54] DNA MOLECULE ENCODING BOVINE GROUP I PHOSPHOLIPASE $A_2$ RECEPTOR

[75] Inventors: Hitoshi Arita, Kawanishi; Osamu Ohara, Toyonaka; Jun Ishizaki, Takarazuka, all of Japan

[73] Assignee: Shionogi & Co., Ltd., Osaka, Japan

[21] Appl. No.: 220,603

[22] Filed: Mar. 30, 1994

[30] Foreign Application Priority Data

| Mar. 30, 1993 | [JP] | Japan | 5-072323 |
| Aug. 20, 1993 | [JP] | Japan | 5-206686 |
| Mar. 10, 1994 | [JP] | Japan | 6-040177 |

[51] Int. Cl.$^6$ ............ C12N 15/12; C07K 14/705
[52] U.S. Cl. ............ 435/69.1; 536/23.5; 435/252.3; 435/254.11; 435/325; 435/365; 435/361; 435/348
[58] Field of Search ............ 435/69.1, 320.1, 435/240.1, 252.3, 254.11, 240.2; 536/23.1, 23.5

[56] References Cited

PUBLICATIONS

Sambrook et al., Molecular Cloning, A Laboratory Manual, sec. Edition, vol. 3, chp 16 pp. 16.2–16.30, 1989 Cold Spring Harbor Laboratory Press.
M. Tohkin et al., "Pancreatic–type Phospholipase $A_2$ Stimulates Prostaglandin Synthesis in Mouse Osteoblastic Cells (MC3T3–E1) via a Specific Binding Site," *J. Biol. Chem.*, 268, pp. 2865–2871 (1993).
H. Arita et al., "Novel Proliferative Effect of Phospholipase $A_2$ in Swiss 3T3 Cells via Specific Binding Site", *J. Biol. Chem.*, 266, pp. 19139–19141 (1991).
K. Hanasaki & H. Arita, "Characterization of a High Affinity Binding Site for Pancreatic–type Phospholipase $A_2$ in the Rat: Its Cellular and Tissue Distribution", *J. Biol. Chem.*, 267, pp. 6414–6420 (1992).
K. Hanasaki & H. Arita, "Purification and Characterization of a High–affinity Binding Protein for Pancreatic–type Phospholipase $A_2$", *Biochim. Biophys. Acta*, 1127, pp. 233–241 (1992).
J. Ishizaki et al., "Molecular Cloning of Pancreatic Group I Phospholipase $A_2$ Receptor", *J. Biol. Chem.*, 269, pp. 5897–5904 (1994).
T. Kanemasa et al., "Contraction of Guinea Pig Lung Parenchyma by Pancreatic Type Phospholipase $A_2$ via Its Specific Binding Site", *FEBS Lett.*, 303, pp. 217–220 (1992).
T. Sakata et al., "Presence of Pancreatic–type Phospholipase $A_2$ mRNA in Rat Gastric Mucosa and Lung", *Biochim. Biophys. Acta*, 1007, pp. 124–126 (1989).
J.J. Seilhamer et al., "Pancreatic Phospholipase $A_2$: Isolation of the Human Gene and cDNAs from Porcine Pancreas and Human Lung", *DNA*, 5, pp. 519–527 (1986).
M. Taylor et al., "Primary Structure of the Mannose Receptor Contains Multiple Motifs Resembling Carbohydrate–recognition Domains", *J. Biol. Chem.*, 265, pp. 12156–12162 (1990).
H. Tojo et al., "A Phospholipase $A_2$ in the Supernatant Fraction of Rat Spleen: Its Similarity to Rat Pancreatic Phospholipase $A_2$", *J. Biol. Chem.*, 263, pp. 5724–5731 (1988).
T. Yasuda et al., "Purification and Characterization of Phospholipase $A_2$ from Rat Stomach", *Biochim. Biophys. Acta*, 1046, pp. 189–194 (1990).
J.J. Seilhamer et al., "Pancreatic Phospholipase $A_2$: Isolation of the Human Gene and cDNAs from Porcine Pancreas and Human Lung", *DNA*, 5, pp. 519–527 (1986).
Duan et al., J. of Biol. Chem., vol. 266, p. 413, 1991.
Hunkapiller et al., Methods In Enzymology, vol. 91, pp. 227–236, 1983, Academic Press.
Wallace et al., Methods In Enzymology, vol. 152 pp. 432–442, 1987, Academic Press.

*Primary Examiner*—Stephen G. Walsh
*Assistant Examiner*—Sally P. Teng
*Attorney, Agent, or Firm*—Fish & Neave; James F. Haley, Jr.

[57] ABSTRACT

The present invention provides a bovine group I phospholipase $A_2$ receptor comprising an amino acid sequence from Leu in the 486 position to Pro in the 940 position of SEQ ID No. 1, and a gene encoding the bovine group I phospholipase $A_2$ receptor. It was found that the bovine group I phospholipase $A_2$ receptor has multi-domain structure.

10 Claims, 6 Drawing Sheets

FIG. 1

```
        1   2   3   4   5   6   7   8   9   10  11  12
       Glu-Thr-Ala-Ala-Trp-Ala-Val-Thr-Pro-Glu-Arg-Leu- (I)  5'-GAG ACC GCN GCN TGG GC-3'
(II) 5'-ACC GCN GCN TGG GCN GT-3'

13  14  15  16  17  18  19   20    21   22  23
       Arg-Glu-Trp-Gln-Asp-Lys-X  - Ile- Phe-Ile- Lys
(III)           3'- CTA TTT ATA TAG AAG TAG TT-5'
                                 G  CGCG (IV) 3'-GTT CTA TTT ATA TAG AAG TA-5'
            C    G    C GCG
```

DNA MOLECULE ENCODING BOVINE GROUP I PHOSPHOLIPASE $A_2$ RECEPTOR

BACKGROUND OF THE INVENTION

1. Field of the Invention

The present invention relates to a bovine group I phospholipase $A_2$ receptor; a structural gene of a bovine group I phospholipase $A_2$ receptor; a bovine group I phospholipase $A_2$ receptor encoded by the structural gene; an expression vector having the structural gene; a transformant having the expression vector; and a method for producing a bovine group I phospholipase $A_2$ receptor using the transformant.

2. Description of the Related Art

Phospholipase $A_2$ (hereinafter referred to as $PLA_2$; EC 3.1.1.4) is a lipolytic enzyme for hydrolyzing a 2-acyl ester bond in 3-sn-phosphoglyceride and is known to be present in mammalian pancreas, snake venom and the like. $PLA_2$ which is known in the art can be classified into a high molecular weight intercellular type and a low molecular weight secretion type. The low molecular weight secretion type $PLA_2$ are further classified into two groups: $PLA_2$-I and $PLA_2$-II. $PLA_2$-I is present in mammalian pancreas and the like. $PLA_2$-I in the pancreas is one of the digestive enzymes secreted in pancreatic juice, and is generally present as a zymogen and transformed into the active form by being hydrolyzed with a proteolytic enzyme such as trypsin. $PLA_2$-II is present in a large amount in platelets and the like, and is regarded to be mainly related to inflammation mechanisms.

Recently it was found that $PLA_2$-I also exists in the lung, stomach, spleen and kidney (Sakata et al., Biochim. Biophys. Acta, 1007, 124–126 (1989); Sellhamer et al., DNA, 5, 519–527 (1986); Yasuda et al., Biochim. Biophys. Acta, 1046, 189–194 (1990); and Tojo et al., J. Biol. Chem., 263, 5724–5731 (1988)). Further, it has been suggested that $PLA_2$-I possibly has another function other than as a digestive enzyme (Kanemasa et al., Biochim. Biophys. Acta, 1125, 210–214 (1992)). It has also been reported that $PLA_2$-I exhibits, through a $PLA_2$-I receptor, a function in the growth of cells (Arita et al., J. Biol. Chem., 266, 19139–19141 (1991)) and in contraction of lung parenchyma (Kanemasa et al., FEBS LETTERS, 303, 217–220 (1992)).

A protein which binds to $PLA_2$-I (i.e., a $PLA_2$-I receptor) was recently identified. This protein was purified from a membrane fraction of a bovine corpus luteum and comprises one glycoprotein having a molecular weight of 190,000 (Hanasaki and Arita, Biochim. Biophys. Acta, 1127, 233–241 (1992)).

SUMMARY OF THE INVENTION

The bovine group I phospholipase $A_2$ receptor of this invention comprises an amino acid sequence from Leu in the 486 position to Pro in the 940 position of SEQ ID No. 11.

In one embodiment, the bovine group I phospholipase $A_2$ receptor comprises an amino acid sequence from Glu in the 1 position to Lys in the 1372 position of SEQ ID No. 11.

In one embodiment, the bovine group I phospholipase $A_2$ receptor comprises an amino acid sequence from Met in the −20 position to Lys in the 1372 position of SEQ ID No. 11.

In one embodiment, the bovine group I phospholipase $A_2$ receptor comprises an amino acid sequence from Glu in the 1 position to Gln in the 1443 position of SEQ ID No. 11.

In one embodiment, the bovine group I phospholipase $A_2$ receptor comprises an amino acid sequence from Met in the −20 position to Gln in the 1443 position of SEQ ID No. 11.

The DNA sequence of this invention encodes any of the above-mentioned bovine group I phospholipase $A_2$ receptors.

In one embodiment, the DNA sequence comprises a base sequence from C in the 1794 position to C in the position of SEQ ID No. 1.

In one embodiment, the DNA sequence comprises a base sequence from G in the 340 position to A in the position of SEQ ID No. 1.

In one embodiment, the DNA sequence comprises a base sequence from A in the 280 position to A in the position of SEQ ID No. 1.

In one embodiment, the DNA sequence comprises a base sequence from G in the 340 position to G in the 4668 position of SEQ ID No. 1.

In one embodiment, the DNA sequence comprises a base sequence from A in the 280 position to G in the 4668 position of SEQ ID No. 1.

The expression vector of this invention has any of the above-mentioned DNA sequences.

The transformant of this invention is obtained by introducing the expression vector into a host.

In one embodiment, the host is a mammalian cell.

The method for producing a bovine group I phospholipase $A_2$ receptor of this invention comprises the steps of: culturing the transformant in a medium; and recovering the produced bovine group I phospholipase $A_2$ receptor from the medium.

Thus, the invention described herein makes possible the advantages of (1) providing a $PLA_2$-I receptor that is useful in the screening of an agonist or an antagonist of the $PLA_2$-I receptor that can be a promising proliferative agent or vasodilator; (2) providing a secretion type $PLA_2$-I receptor and a low molecular weight type $PLA_2$-I receptor, each of which is a fragment of the $PLA_2$-I receptor and is useful in various experiments such as screening of an agonist or an antagonist of the $PLA_2$-I receptor owing to its solubility in an ordinary buffer solution; (3) providing a secretion type $PLA_2$-I receptor and a low molecular weight type $PLA_2$-I receptor, each of which is useful as a $PLA_2$-I inhibitor or the like because it has no membrane binding site and does not transmit information to cells even when it bonds to the $PLA_2$-I; (4) providing a low molecular weight type $PLA_2$-I receptor which is useful in analysis of the interaction between a receptor and a ligand including screening of an agonist or an antagonist because it has few regions that are unnecessary for a binding with the $PLA_2$-I; (5) providing an efficient production method for a secretion type $PLA_2$-I receptor and a low molecular weight type $PLA_2$-I receptor in which they can be purified with more ease than a wild type receptor; (6) providing a DNA sequence encoding each of the above-mentioned $PLA_2$-I receptors; (7) providing an expression vector having the DNA sequence; (8) providing a transformant having the expression vector; and (9) providing a method for producing each of the $PLA_2$-I receptors by using the transformant.

These and other advantages of the present invention will become apparent to those skilled in the art upon reading and understanding the following detailed description with reference to the accompanying figures.

BRIEF DESCRIPTION OF THE DRAWINGS

FIG. 1 shows an N-terminal amino acid sequence of a $PLA_2$-I receptor derived from a membrane fraction of bovine corpus luteum (SEQ ID NO:8) and DNA oligomer sequences of PCR primers for producing a probe: (I) (SEQ ID NO:2); (II) (SEQ ID NO:3); (III) (SEQ ID NO: 4) and (IV) (SEQ ID NO: 5).

DESCRIPTION OF THE PREFERRED EMBODIMENTS

Figure 2:
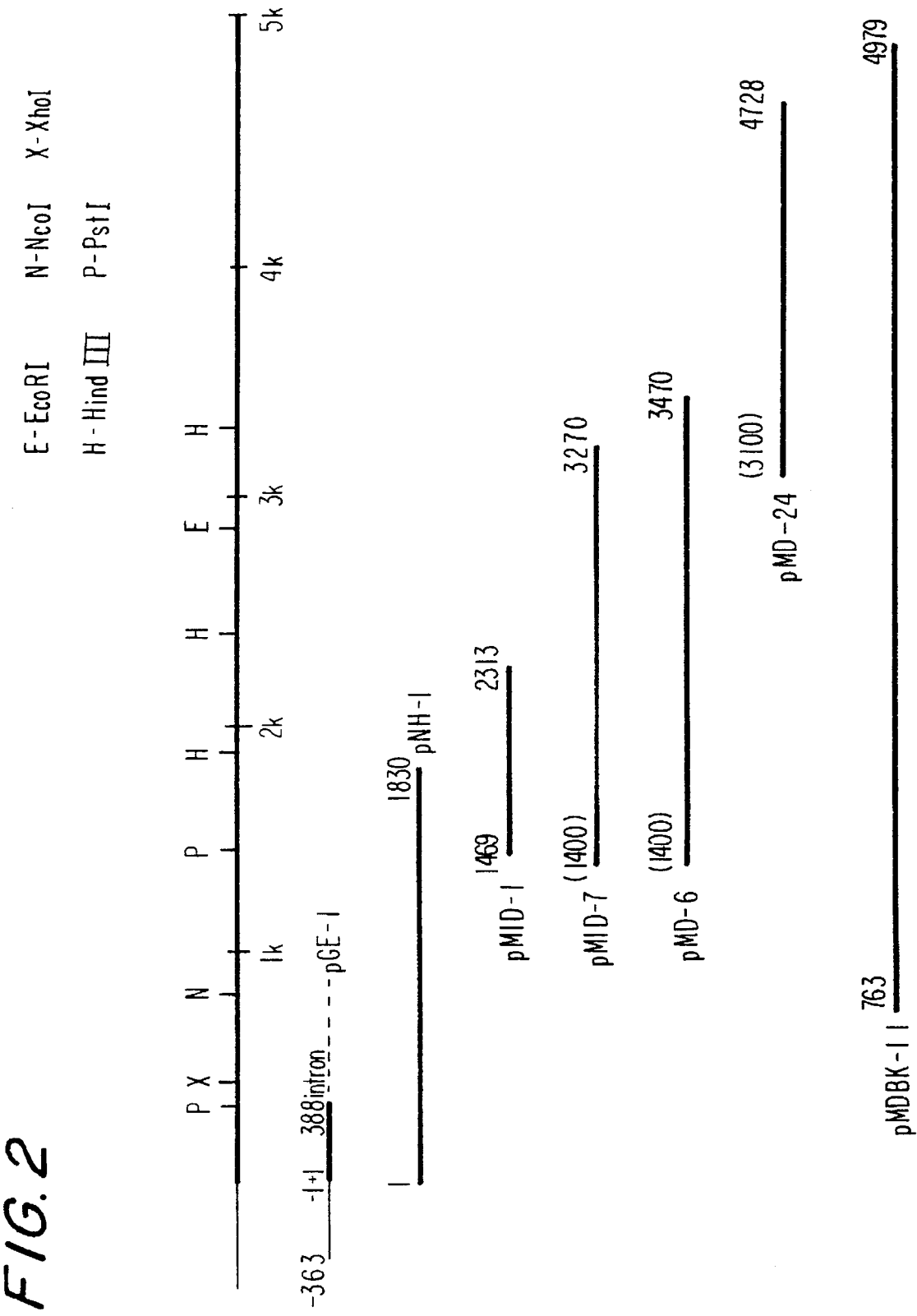
FIG. 2 shows a position of each clone encoding part of a $PLA_2$-I receptor of the present invention and a restriction map.

The present inventors have made various studies to determine the amino acid sequence of a bovine group I $PLA_2$ receptor protein purified from a bovine corpus luteum and to determine a DNA sequence encoding the protein based on the amino acid sequence. As a result, they found a DNA sequence encoding the bovine group I $PLA_2$ receptor protein in a cDNA library derived from a bovine placenta and a cDNA library derived from bovine kidney cells. The protein was transmembrane protein, and the region on the amino terminal side existing outside of the cell membrane was assumed to be a $PLA_2$-I recognition site. Thus, the inventors were able to produced cDNA by removing a region encoding the sequence on the carboxyl terminal side from the $PLA_2$-I receptor cDNA. The cDNA obtained was used to express a secretion type $PLA_2$-I receptor. Further, the inventors were able to specify a $PLA_2$-I binding site and produce DNA encoding the binding site alone. The DNA was used to express a low molecular weight type $PLA_2$-I receptor. In this way, the present invention was attained.

The present invention may be described by the following procedures:

(1) Sequencing of DNA encoding a $PLA_2$-I receptor protein:

The sequence of a DNA fragment including DNA encoding a $PLA_2$-I receptor protein of the present invention is determined as follows: A cDNA library derived from, for example, a bovine placenta, is subjected to screening with a probe. The obtained DNA is analyzed through DNA sequencing to determine the sequence.

(A) Production of a DNA probe:

A gene encoding the $PLA_2$-I receptor protein can be obtained from a cDNA library derived from, for example, a bovine placenta. The following is an example of the production method for a probe to be used in the cloning of the gene encoding the $PLA_2$-I receptor protein from the bovine placenta cDNA library:

A peptide sequence at the amino terminal portion of the $PLA_2$-I receptor protein is determined as follows: The $PLA_2$-I receptor protein is purified from, for example, a membrane fraction of a bovine corpus luteum, to homogeneity through a series of separations (Hanasaki, K., Biochim. Biophys. Acta, 1127, 233–241 (1992)). The purified $PLA_2$-I receptor protein is analyzed by using, for example, an Applied Biosystems 477A Protein Sequencer. As a result, the amino acid sequence at the amino terminal portion of the purified $PLA_2$-I receptor protein is determined as shown in FIG. 1 and SEQ ID No. 8 of the accompanying sequence listing.

A probe for cloning the gene encoding the $PLA_2$-I receptor protein can be directly or indirectly produced based on the amino acid sequence at the amino terminal portion.

An example of the indirect production of the probe is as follows: A DNA primer for the polymerase chain reaction (PCR) is synthesized based on the amino acid sequence at the amino terminal. A template for PCR prepared as described below can be amplified by using the DNA primer to obtain the probe for screening. The template for PCR can be DNA obtained from a bovine corpus luteum, where the $PLA_2$-I receptor protein is considered to be present in a large amount. Such DNA can be obtained, for example, by extracting RNA from a bovine corpus luteum by the guanidine thiocyanate method (Chomczynski, P. et al., Anal. Biochem., 162, 156–159 (1987)), and by preparing cDNA from the extracted RNA. The cDNA is prepared from the RNA by annealing a primer with the RNA and synthesizing the DNA from the primer by using a reverse transcriptase. At this point, for example, a SuperScript Plasmid System for cDNA and Plasmid Cloning (BRL, U.S.A.) can be used.

The PCR is performed in accordance with the description in, for example, Science, 239, 487–491 (1988), and an automated PCR device (Perkin Elmer Cetus, U.S.A.) can be used.

The probe thus obtained can then be labeled for use in the subsequent screening described below.

(B) Screening of a library:

Various libraries derived from bovine sources can be used as a library for screening the DNA encoding the bovine group I $PLA_2$ receptor. Examples of the library include a bovine chromosome library, a bovine placenta cDNA library and a bovine kidney cell cDNA library.

The library is screened by a known method by using the probe obtained in item (A). Examples of the screening method include the plaque hybridization of recombinant phage plaque and the colony hybridization of recombinant E. coli.

(C) Determination of the base sequence of a clone:

The base sequence of an insert of the clone obtained by screening the library is determined as follows: The clone is cleaved at a restriction site in the clone, and each of the obtained DNA fragments is subjected to cloning with an appropriate sequence vector such as M13mp18 (Takara Shuzo, Japan) and M13mp19 (Takara Shuzo, Japan). Then, the base sequence of the cloned fragment is determined by the dideoxy method (Sanger, F., Science, 214, 1205–1210 (1981)). SEQ ID No. 1 of the accompanying sequence listing shows the sequence of the DNA including the gene encoding the PLA$_2$-I receptor protein which is determined by analyzing the clone. SEQ ID No. 1 shows the sequence of the entire gene encoding the PLA$_2$-I receptor protein.

(2) Expression of a recombinant type PLA$_2$-I receptor protein:

The gene encoding the PLA$_2$-I receptor protein of the present invention can be inserted into an appropriate vector to work as an expression vector for expressing the PLA$_2$-I receptor protein.

Such an expression vector is introduced into, for example, bacterium, yeast, an insect cell or an animal cell to produce a transformant. The PLA$_2$-I receptor protein of the present invention can be produced by culturing the transformant.

For example, the PLA$_2$-I receptor protein can be produced as follows: An expression vector, in which the gene encoding the PLA$_2$-I receptor protein of the present invention is located downstream to pSVL SV40 late promoter, is introduced into COS7 cells derived from a monkey, thereby producing a transformant. The transformant is cultured in the presence of 5% $CO_2$ at a temperature of 37° C. for several days.

Figure 4:
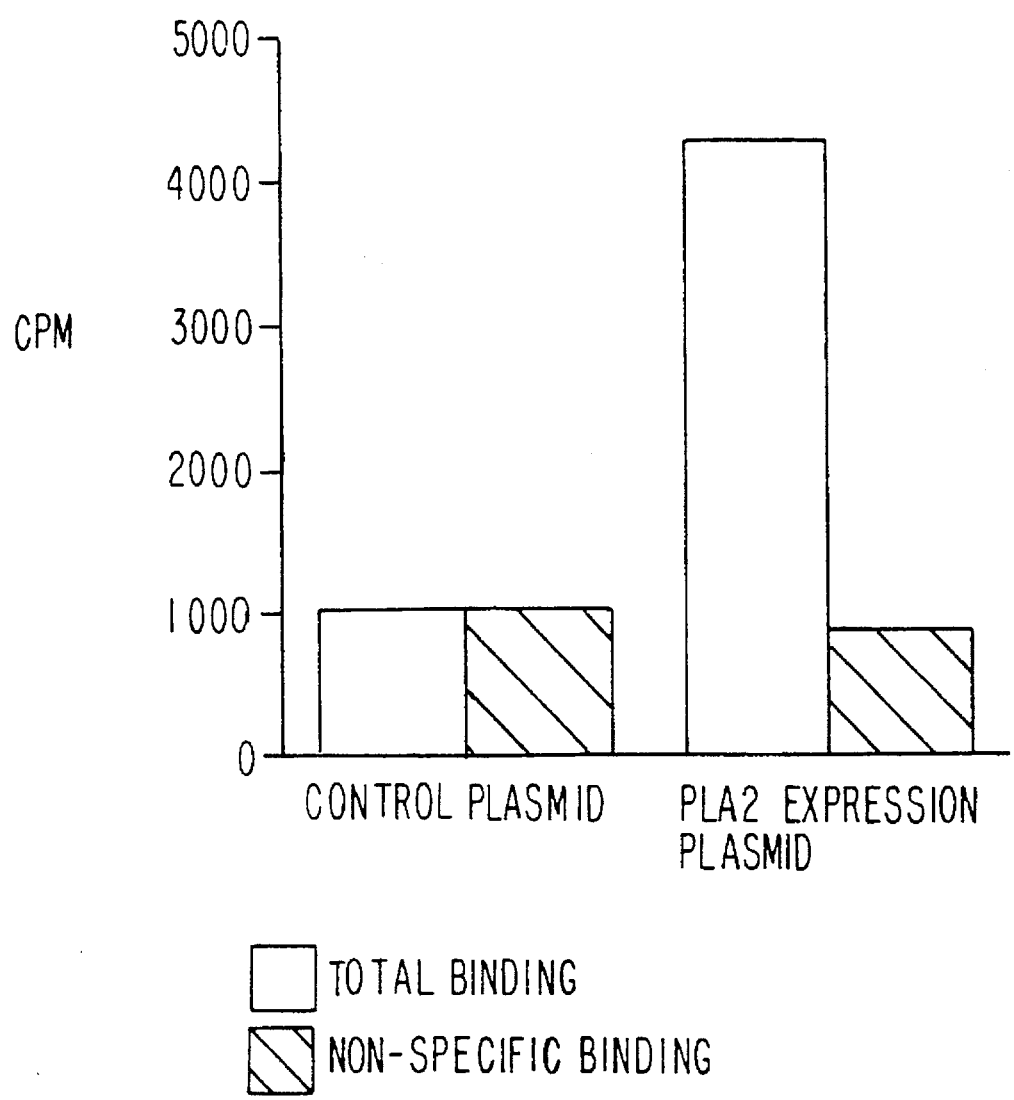
FIG. 4 shows the binding ability to $PLA_2$-I of a transformant having a gene encoding the $PLA_2$-I receptor of the present invention and a control transformant not having the gene.

The culture for producing the PLA$_2$-I receptor protein is centrifuged to collect the cultured cells in the precipitated fraction. The collected cells are washed, and a PLA$_2$-I labeled with a $^{125}$I radioisotope is added thereto to cause a binding reaction between the PLA$_2$-I and the PLA$_2$-I receptor. By measuring the specific binding of the PLA$_2$-I, the amount of the PLA$_2$-I receptor protein expressed on the cells can be determined. The same procedure is repeated with regard to a control culture including no gene encoding the PLA$_2$-I receptor protein. The results are shown in FIG. 4, which will be described in detail below.

(3) Expression of a secretion type PLA$_2$-I receptor protein:

In the PLA$_2$-I receptor protein of the present invention, a protein that does not include a membrane binding site, that is, an amino acid sequence from Gly in the 1373 position toward the carboxyl terminal in SEQ ID No. 11 is classified as a secretion type protein. Such a protein is referred to as the secretion type PLA$_2$-I receptor protein. The secretion type PLA$_2$-I receptor protein can be produced by using a DNA oligomer including mismatching. The cDNA of the oligomer is obtained by removing, for example, an amino acid sequence from the 1373 position toward the carboxyl terminal in SEQ ID No. 11 from the entire gene encoding the PLA$_2$-I receptor protein of the present invention.

The cDNA is inserted into an appropriate vector in the same manner as in the entire gene encoding the PLA$_2$-I receptor protein of the present invention, and the vector can work as an expression vector for expressing the secretion type PLA$_2$-I receptor protein.

Such an expression vector is introduced into, for example, bacterium, yeast, an insect cell and an animal cell to produce a transformant. For example, the expression vector is introduced into COS7 cells derived from a monkey to produce a transformant. By culturing the transformant, a secretion type PLA$_2$-I receptor protein that has a PLA$_2$-I binding ability and is liberated through the cell membrane into the medium can be produced. Further, the secretion type PLA$_2$-I receptor protein can be constantly expressed by inserting the expression vector into a chromosome of a CHO cell.

(4) Expression of a low molecular weight type PLA$_2$-I receptor protein:

In the PLA$_2$-I receptor protein of the present invention, a protein mainly comprising an amino acid sequence from Leu in the 486 position to Pro in the 940 position of SEQ ID No. 11, which is a PLA$_2$-I binding site, is referred to as the low molecular weight type PLA$_2$-I receptor protein. A gene encoding the low molecular weight type PLA$_2$-I receptor protein can be prepared by cleaving, with an appropriate restriction enzyme, a DNA fragment including the PLA$_2$-I binding site, that is, an amino acid sequence from the 486 position to the 940 position of SEQ ID No. 11, from the entire gene encoding the PLA$_2$-I receptor protein of the present invention. Such a DNA fragment is inserted into an appropriate vector in the same manner as in the gene encoding the PLA$_2$-I receptor protein and the secretion type PLA$_2$-I receptor protein. The vector can work as an expression vector for expressing the low molecular weight type PLA$_2$-I receptor protein.

Such an expression vector is introduced into, for example, bacterium, yeast, an insect cell and an animal cell to produce a transformant. By culturing the transformant, the low molecular weight type PLA$_2$-I receptor protein of the present invention can be produced. For example, an expression vector of the low molecular weight type PLA$_2$-I receptor protein is introduced into COS7 cells derived from a monkey to produce a transformant. By culturing the transformant, the low molecular weight type PLA$_2$-I receptor protein having a PLA$_2$-I binding ability can be produced in the supernatant of the medium. Further, the low molecular weight type PLA$_2$-I receptor protein can be constantly expressed by inserting the expression vector into a chromosome of a CHO cell.

EXAMPLES

The present invention will now be described in more detail by way of examples.

The following general molecular biological experiments used in the present invention were performed in accordance with Molecular Cloning (Cold Spring Harbor Laboratory, N.Y., 1982): agarose gel electrophoresis of DNA; polyacrylamide gel electrophoresis; collection of electrophoresed DNA from gel through a dialysis membrane; extraction with phenol; extraction with chloroform; precipitation with ethanol; ligation; transformation of *E. coli*; cultivation of recombinant *E. coli*; preparation of plasmid DNA; preparation of phage DNA; cleavage of DNA with a restriction enzyme; and labeling of DNA. Reagents used in these experiments such as a restriction enzyme and a DNA modification reagent were purchased from Takara Shuzo, Japan if not mentioned otherwise.

EXAMPLE 1

A. Determination of the amino acid sequence of a peptide at the amino terminal of a PLA$_2$-I receptor protein:

In the cloning of a gene, a DNA fragment is required to detect and identify the objective gene. In order to obtain such a DNA fragment, the present inventors sought to obtain information to determine the base sequence of the DNA based on the amino acid sequence of the peptide at the amino terminal portion of a purified PLA$_2$-I receptor protein.

First, 15 μg of the PLA$_2$-I receptor protein, which was purified into homogeneity from a membrane fraction of a bovine corpus luteum through a series of sepations using diethylaminoethyl-Sephacel chromatography, the PLA$_2$-I-affinity gel chromatography and gel filtration HPLC (Hanasaki, K. et al., Biochim. Biophys. Acta, 1127, 233–241 (1992)), was desalted with Centricon 100 (Amicon, U.S.A.). The resultant material was dissolved in a solution including 10 mM HCl and 20 mM octylthioglucoside, and the obtained solution was analyzed by using an Applied Biosystems 477A Protein Sequencer. As a result, an amino acid sequence of 23 amino acids was determined as shown in FIG. 1 and SEQ ID No. 8 of the accompanying sequence listing.

B. Synthesis of DNA corresponding to the 23 residues at the amino terminal:

A DNA oligomer was synthesized based on the amino acid sequence determined in item A, and a DNA probe to be used in the screening of a gene library described below was produced by PCR (Saiki, R. K. et al., Science, 239, 487–494 (1988)). The DNA oligomer used in the PCR was designed and produced as follows: A mixed DNA oligomer covering the entire DNA sequence that can encode a certain region of a determined amino acid sequence can be designed by using codons corresponding to each of the amino acid residues. Specifically, codons preferentially used in a mammal were used to synthesize DNA oligomers (I) (SEQ ID No. 2), (II) (SEQ ID No. 3), (III) (SEQ ID No. 4) and (IV) (SEQ ID No. 5) based on the sequences on the amino terminal side and the carboxyl terminal side of the sequence of FIG. 1. Among the above, DNA oligomers (III) and (IV) were based on the base sequence of the complementary chain of the gene encoding the protein. Since these DNA oligomers were short, a nucleic acid synthesizer (Pharmacia LKB Gene Assembler Plus, DNA Synthesizer) was used. Since these DNA oligomers were positioned as shown in FIG. 1, it was considered that PCR by using an appropriate specimen as a template would amplify 65 base pairs of the $PLA_2$-I receptor cDNA fragment from the combination of oligomers (I) and (IV) and 62 base pairs from the combination of oligomers (II) and (IV). Further, the product amplified from the combination of oligomers (I) and (IV) was purified by gel electrophoresis to collect DNA having a length of 65 base pairs. Then the collected DNA was used as a template in another PCR using oligomers (II) and (IV), resulting in obtaining $PLA_2$-I receptor cDNA more specifically.

C. Preparation of a template to be used in the PCR:

Since a bovine corpus luteum contains a larger amount of $PLA_2$-I receptor protein than other organs, the bovine corpus luteum was regarded to be suitable as a material for gene cloning. RNA was extracted from seven bovine corpus lutea frozen in a fresh state by the guanidine thiocyanate method (Chomczynski, P. et al., Anal. Biochem., 162, 156–159 (1987)).

The chain length of the $PLA_2$-I receptor cDNA was expected to be at least 4500 bases when calculated from the molecular weight of the receptor protein. It is known to be difficult to obtain such a long cDNA with a complete length by a general preparation method by using an oligo dT primer.

Therefore, the present inventors attempted using, as a primer for preparation of cDNA, a DNA oligomer in the downstream vicinity of the region to be amplified by the PCR. The DNA oligomer used is shown as oligomer (III) in FIG. 1. Specifically, the cDNA was prepared from 10 μg of bovine corpus luteum RNA by using 1 pmole of the DNA oligomer (III) as a primer. In the preparation of the cDNA, the cDNA synthesizing reaction system of the SuperScript Plasmid System for cDNA and Plasmid Cloning (BRL, U.S.A.) was used.

D. Amplification and isolation of the $PLA_2$-I receptor cDNA by PCR:

By using the DNA oligomers (I) and (IV) obtained in item B, the $PLA_2$-I receptor cDNA was amplified by PCR using the cDNA specimen obtained in item C as a template. In the PCR, an AmpliTaq DNA polymerase (Perkin Elmer Cetus, U.S.A.) was used as an enzyme, a reaction solution of which was prepared according to the accompanying instructions. A thermal cycler (Perkin Elmer Cetus, U.S.A.) was used for the amplification. A cycle of one minute at 94° C. and one minute at 37° C. was repeated 15 times, and successively a cycle of one minute at 94° C., one minute at 50° C. and fifteen seconds at 72° C. was repeated 15 times. After the amplification, 200 μl of the PCR reaction solution was subjected to extraction with chloroform, precipitation with ethanol, and 15% polyacrylamide gel electrophoresis, thereby separating the amplified product according to molecular weight. A gel fragment corresponding to the 65 base pairs, where the $PLA_2$-I receptor cDNA was expected to be amplified, was taken out, and DNA in the gel fragment was collected. Then, PCR using the collected DNA as a template was performed again by using the oligomers (II) and (IV). This time, a cycle of one minute at 94° C., one minute at 50° C. and one minute at 72° C. was repeated 30 times for the amplification. The PCR product was also subjected to extraction with chloroform, precipitation with ethanol and polyacrylamide gel electrophoresis to collect DNA corresponding to the 62 base pairs. The obtained double-stranded DNA was inserted into an appropriate cloning vector for cloning in *E. coli*. Specifically, the isolated DNA was ligated with a cloning vector pBLUE SCRIPT(KS-) (Stratagene, U.S.A.), which were previously made linear with a restriction enzyme EcoRV and mixed with dideoxythymidine (Holton, T. A. et al., Nucleic Acids. Res., 19, 1156 (1991)), thereby inserting the DNA into the cloning vector. The obtained ligation solution was subjected to extraction with phenol and precipitation with ethanol for purification. The purified ligation solution was used to transform *E. coli* C600 strain (Clonetech, U.S.A.). The transformed *E. coli* was selected in an LB agar medium including 50 μg/ml of ampicillin. With regard to six strains of the obtained transformant, a plasmid DNA included in the *E. coli* was prepared. With regard to four strains of them, the base sequence of the PCR product inserted at the EcoRV cleavage site of the plasmid DNA was determined by the dideoxy method (Sanger, F., Science, 214, 1205–1210 (1981)). The determined base sequence of two clones among them was found to encode an amino acid sequence between the oligomers (II) and (IV) in FIG. 1.

EXAMPLE 2

Screening of a Bovine Chromosome Library

The $PLA_2$-I receptor cDNA fragment obtained by the PCR in item D of Example 1 can be used as a probe for screening a general gene library. This probe was, however, inferior in specificity, and therefore, a longer probe was desired. Further, the expression frequency of the $PLA_2$-I receptor gene was expected to be comparatively low. Therefore, instead of the cDNA library, a chromosome library that was expected to contain the entire gene region uniformly and to be independent of its expression frequency was first screened to isolate a longer cDNA fragment.

The chromosome library used was a Bovine Genomic Library purchased from Clonetech, U.S.A. The cDNA fragment obtained in item D of Example 1 was labeled with a $^{32}P$ radioisotope to be used as a probe. The screening was performed in accordance with the protocol attached to the library. The specific procedure was as follows: The titer of a phage solution was first measured, and the phage solution in an amount sufficient to form approximately 40,000 phage plaques per one plate was mixed with *E. coli* host attached to the library. The mixture was then spread on an LB plate with a size of 10×15 cm. The plate was cultured overnight at a temperature of 37° C. The plaques formed in this manner were screened by plaque hybridization.

One positive clone (shown as pGE-1 in FIG. 2) was obtained through the screening of approximately 800,000 clones. As a result of the analysis of the base sequence of the positive clone, it was found to contain a base sequence from the 1 position to the 388 position of SEQ ID No. 1. It was also found to have an intron downstream to the base in the 388 position as shown with a broken line in FIG. 2.

EXAMPLE 3

Screening of a Bovine Placenta cDNA Library

Based on the base sequence determined in Example 2, DNA oligomers that can amplify 128 base pairs from the 257 position to the 384 position of SEQ ID No. 1 by PCR were synthesized as primers (SEQ ID Nos. 6 and 7). The DNA fragment including the 128 base pairs was specifically amplified by PCR using the DNA of the positive clone (pGE-1) obtained in Example 2 as a template. The product was labeled with a $^{32}P$ radioisotope to be used in the screening of a bovine placenta cDNA library. The used library was a Bovine Placenta cDNA Library (5' Stretch) purchased from Clonetech, U.S.A. The screening of the library was performed in accordance with the protocol attached to the library. Specifically, the procedure was similar to that of the screening of the chromosome library described in Example 2. As a result of the screening of approximately 640,000 clones, a clone including a $PLA_2$-I receptor cDNA fragment shown as pNH-1 in FIG. 2 was obtained. The cDNA of the obtained clone was cleaved with a restriction enzyme, separated by gel electrophoresis, and labeled with a $^{32}P$ radioisotope, thereby preparing a DNA probe. The obtained probe was used to screen the same kind of library again (approximately 3,500,000 clones), resulting in isolating clones encoding the genes further downstream to the clone pNH-1. The clones are shown as pMID-1 and pMID-7 in FIG. 2. In this manner, a new DNA probe was prepared from the clone obtained in the preceding screening. Thus, some clones each of which partially encodes the same region were obtained by repeating PCR.

EXAMPLE 4

Screening of an MDBK Cell cDNA Library Derived from a Bovine Kidney

The amount of the $PLA_2$-I receptor expressed in various cultured cells and tissues was measured by the Scatchard plot analysis. As a result, an MDBK cell strain derived from a bovine kidney (ATCC CCL 22) was found to express the $PLA_2$-I receptor in a larger amount than the cells derived from the other organs. By using the cDNA obtained in Example 3 as a probe, the MDBK cell strain cDNA library was screened. The library used was Bovine Kidney cDNA Library in the Lambda ZAPII Vector (Stratagene, U.S.A.). As a result, a plurality of positive clones including pMD-6 and pMD-24 shown in FIG. 2 were obtained.

In addition to the commercially available library, cDNA was synthesized from RNA extracted from the MDBK cells to produce another cDNA library by the SuperScript Plasmid System for cDNA and Plasmid Cloning (BRL, U.S.A.). A plurality of clones including pMDBK-11 shown in FIG. 2 were obtained from this library.

EXAMPLE 5

Determination of the Entire Primary Structure of the $PLA_2$-I Receptor cDNA From the information of the base sequences of pNH-1 and pMDBK-11 among the cDNA clones obtained in Example 4, the entire base sequence of the $PLA_2$-I receptor cDNA was determined. The determined base sequence and the amino acid sequence are shown in SEQ ID No. 1 of the accompanying sequence listing. The cDNA comprises 4978 base pairs in all, including 279 base pairs upstream of ATG, which is regarded as a translation initiation point, 4389 base pairs encoding the $PLA_2$-I receptor protein, and 310 base pairs downstream to the termination codon (including a poly A tail at the 3' terminal of mRNA). Moreover, a cDNA fragment encoding the entire $PLA_2$-I receptor protein could be produced by ligating the cDNA fragments, pNH-1 and pMDBK-11, with each other, which were previously cleaved with a restriction enzyme NcoI (described in detail below).

Based on the sequence of the region encoding the protein, the number of the amino acids of the receptor protein was found to be 1463. A Signal peptide-like sequence, however, was found at the amino terminal portion, and the amino acid sequence at the amino terminal portion of the purified protein (FIG. 1) was found from the 21 position downward in the amino acid sequence of SEQ ID No. 11. Therefore, the 20 residues at the amino terminal portion were presumed to be a signal peptide, and the number of the amino acids of the mature receptor protein after the cleavage of the signal peptide was assumed to be 1443.

The signal peptide is considered responsible for the transportation of the $PLA_2$-I receptor protein synthesized in cells and for its location against the membrane. The binding ability of the protein to the $PLA_2$-I is believed to be due to the 1443 amino acids.

Figure 3:
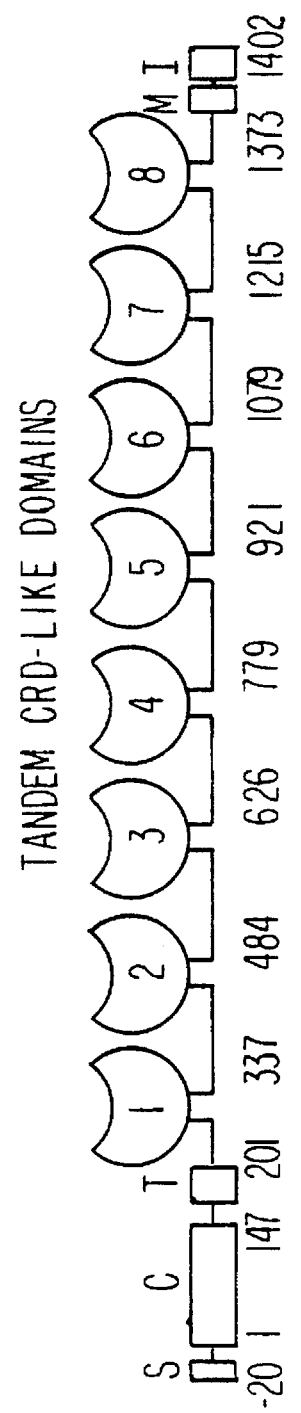
FIG. 3 is a diagram of the domain structure of a $PLA_2$-I receptor estimated based on its homology with a mannose receptor. The numerals in FIG. 3 indicate the numbers of the amino acid residues at the amino terminal in the respective domains (corresponding to SEQ ID NO: 11). As shown, the $PLA_2$-I receptor protein is considered to comprise, in order from the amino terminal, a sequence (S), a domain including a large number of cysteine residues (C), a fibronectin type 2 repeat-like domain (T), eight carbohydrate recognition domain-like domains (CRD1 through CRD8; shown as 1 through 8 in FIG. 3), a membrane binding region (M), and an introcellular domain (I).

Furthermore, the homology in the primary structures with the known proteins in a data bank was searched. As a result, the $PLA_2$-I receptor protein was found to have the highest homology (29% in the primary structure) with a mannose receptor, which is one of the lectins, as compared with the other proteins in the data bank. The homology between them was found in the entire primary structure, and especially in the position of a cysteine residue, which is significant in the definition of the steric structure of a protein. The mannose receptor protein is reported to have a multi-domain structure (Taylor, M. E. et al., J. Biol. Chem., 265, 12156–12162 (1990)). The domain structure of the $PLA_2$-I receptor protein was estimated based on that of the mannose receptor protein. FIG. 3 shows the estimated domain structure of the $PLA_2$-I receptor protein. The numerals in FIG. 3 indicate the numbers of the amino acid residues at the amino terminal in the respective domains (corresponding to SEQ ID No. 11). As shown in FIG. 3, the $PLA_2$-I receptor protein is considered to comprise, in the order from the amino terminal, a signal sequence (S), a domain including a large number of cysteine residues (C), a fibronectin type 2 repeat-like domain (T), eight carbohydrate recognition domain-like domains (CRD1 through CRD8; shown as 1 through 8 in FIG. 3), a membrane binding region (M), and an introcellular domain (I).

EXAMPLE 6

Expression of a Recombinant Type $PLA_2$-I Receptor Protein

It was found that cDNA clones pNH-1 and pMDBK-11 did not have a sequence to be cleaved with an restriction enzyme NcoI except for the NcoI cleavage site shown in FIG. 2 (corresponding to the base sequence in the 799 position of SEQ ID No. 1). Therefore, these clones were cleaved with the restriction enzyme NcoI and subjected to gel electrophoresis for separation and purification of the region upstream to the NcoI cleavage site in the pNH-1 and the region downstream to the NcoI cleavage site in the pMDBK-11. The two obtained cDNA fragments were ligated with each other through the ligation reaction. The ligated DNA fragment is referred to as a PLA$_2$-I receptor cDNA. The PLA$_2$-I receptor cDNA was inserted into a position downstream to the promoter of a pSVL SV40 late promoter expression vector (Pharmacia LKB), which is an expression vector for animal cells. Such a plasmid vector is referred to as a PLA$_2$-I receptor expression vector. Then, COS7 cells derived from a monkey were transfected with the PLA$_2$-I receptor expression vector. In the transfection, a Lipofectin Reagent (GIBCO/BRL Life Technologies, Inc., U.S.A.) was used, and the transfection was performed in accordance with the protocol of the reagent. Three days after the transfection, the COS7 cells were analyzed as follows:

The cultured cells were washed and subjected to the incubation with PLA$_2$-I labeled with a $^{125}$I radioisotope, thereby causing a binding reaction between the PLA$_2$-I and the PLA$_2$-I receptor. Free PLA$_2$-I that did not bind to the receptor was removed by washing, and the amount of the radioisotope on the cell membrane was measured. The same procedure was repeated with regard to cells transfected with a control vector having no PLA$_2$-I receptor cDNA. The results are shown in FIG. 4, with the data being represented as the mean of three experiments. The amount of the radioisotope after the binding reaction between the PLA$_2$-I and the PLA$_2$-I receptor in the presence of a largely excessive amount of unlabeled PLA$_2$-I is regarded to indicate non-specific binding (shown with oblique lines in FIG. 4). By subtracting the amount of the non-specific binding from the measured total binding amount (shown with dots in FIG. 4), the amount of specific binding of the PLA$_2$-I receptor can be obtained. In other words, a PLA$_2$-I binding ability can be indicated as a difference between the total binding and the non-specific binding. As is apparent from FIG. 4, the cells transfected with the PLA$_2$-I receptor expression vector had a significantly high PLA$_2$-I binding ability. In this manner, the cDNA was confirmed to encode the PLA$_2$-I receptor having a high PLA$_2$-I binding ability. The PLA$_2$-I binding ability was measured in accordance with the description in the above-mentioned paper (Hanasaki, K. et al., Biochim. Biophys. Acta, 1127, 233–241 (1992)).

EXAMPLE 7

Expression of a Secretion Type PLA$_2$-I Receptor

A DNA oligomer having a sequence of SEQ ID No. 9 was synthesized to change the cDNA sequence encoding Gly at the 1373 position of SEQ ID No. 11 (GGA) into TGA, the termination codon. The DNA oligomer comprised a sequence of 15 bases corresponding to 5 amino acids from Lys in the 1368 position to Lys in the 1372 position, a sequence for changing the codon encoding Gly in the 1373 position into the termination codon TGA, and a sequence for introducing GCGGCCGC, which is an NotI cleavage site, on the 3' terminal side of the termination codon. This DNA oligomer and another DNA oligomer, which was positioned upstream to a restriction enzyme XbaI recognition sequence (i.e., the base sequence in the 4178 position of SEQ ID No. 1) and corresponded to a sense strand, were used in PCR performed by using the PLA$_2$-I receptor cDNA as a template in a similar manner as in item D in Example 1. The cDNA obtained by the PCR amplification was cleaved with the restriction enzymes XbaI and NotI. The PLA$_2$-I receptor expression vector of Example 6 was cleaved with the restriction enzymes XbaI and NotI to remove the region on the 3' terminal side from the XbaI recognition sequence of the PLA$_2$-I receptor cDNA to prepare a second cDNA. The cDNA fragment amplified by the PCR was inserted into the second cDNA to obtain a vector DNA, which is referred to as a secretion type PLA$_2$-I receptor expression vector. In the secretion type PLA$_2$-I receptor expression vector, the sequence encoding Gly in the 1373 position of the PLA$_2$-I receptor cDNA was replaced with a termination codon, and the secretion type PLA$_2$-I receptor cDNA did not include a region encoding the amino acids from the 1374 position downward.

Figure 5:
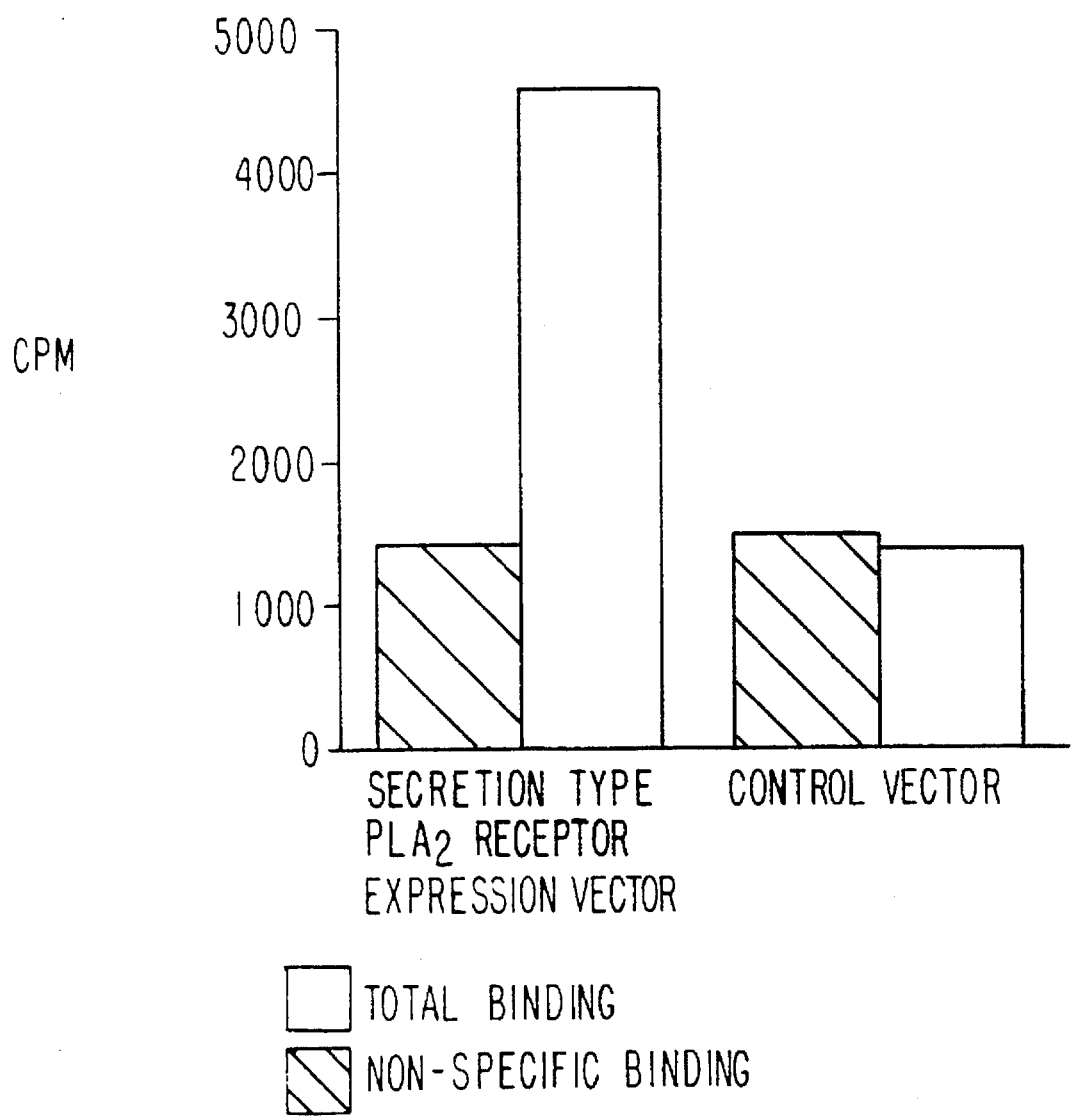
FIG. 5 shows the binding ability in a 200 μl medium three days after the transfection of COS cells with a secretion type $PLA_2$-I receptor expression vector of the present invention and that with a control vector having no $PLA_2$-I receptor cDNA.

COS7 cells derived from a monkey were transfected with the secretion type PLA$_2$-I receptor expression vector. The PLA$_2$-I binding ability of the supernatant of the medium was measured by the method in which the PLA$_2$-I and the receptor protein were coprecipitated with polyethylene glycol ( Hanasaki, K. et al., J. Biol. Chem., 267, 6414–6420 (1992)). The same procedure was repeated with regard to cells transfected with a control vector including no PLA$_2$-I receptor cDNA. The results are shown in FIG. 5, where the amount of non-specific binding is indicated with a mesh and the amount of total binding is indicated with dots. As is apparent from FIG. 5, the cells transfected with the secretion type PLA$_2$-I receptor expression vector have a significantly higher PLA$_2$-I binding ability as compared with those transfected with the control vector. Furthermore, it was found that a recombinant type receptor expressed from the secretion type PLA$_2$-I receptor expression vector was secreted into a medium, and had a PLA$_2$-I binding affinity (Kd=0.8 nM) as high as that of a wild type receptor.

EXAMPLE 8

Expression of a Low Molecular Weight Type PLA$_2$-I Receptor Protein Comprising the Domains CRD3 through CRD5

The PLA$_2$-I receptor cDNA of Example 6 was cleaved with restriction enzymes StuI and Pf1MI to prepare a DNA fragment comprising a sequence from the StuI cleavage site in the 1794 position to the Pf1MI cleavage site in the 3165 position of the base sequence shown in SEQ ID No. 1, and its termini were blunt ended with E. coli DNA polymerase I (Klenow fragment). The DNA fragment obtained in this manner was ligated through a ligation reaction with a vector DNA obtained by cleaving the PLA$_2$-I receptor expression vector of Example 6 with restriction enzymes XhoI and XbaI and blunt ending its termini. The vector DNA obtained through the ligation is referred to as a low molecular weight type PLA$_2$-I receptor expression vector. The PLA$_2$-I receptor cDNA moiety of the low molecular weight type PLA$_2$-I receptor expression vector did not include base sequences from the 426 position to the 1793 position and from the 3162 position to the 4176 position, which are included in a wild type PLA$_2$-I receptor cDNA. Moreover, since the codon encoding an amino acid in the 29 position was changed from GAG into GAC through the ligation, Asp was encoded here. Similarly, an amino acid in the 941 position was changed into Asn. In addition, since TAG at the XbaI cleavage site from the 4176 position to the 4181 position worked as a termination codon as a result of the ligation, the cDNA moiety from the 4178 position downward of the base sequence was not translated into a protein. Therefore, the translated region corresponded to amino acid sequences from the −20 position to the 28 position and from the 486 position to the 940 position of SEQ ID No. 11, and Asp and Asn were attached between the 28 position and the 486 position and to the carboxyl terminal side in the 940 position, respectively. SEQ ID No. 10 shows the amino acid sequence of the expressed low molecular weight type $PLA_2$-I receptor. The low molecular weight type $PLA_2$-I receptor includes the entire domains CRD3 through CRD5 of the $PLA_2$-I receptor, but scarecely includes the other domains.

Figure 6:
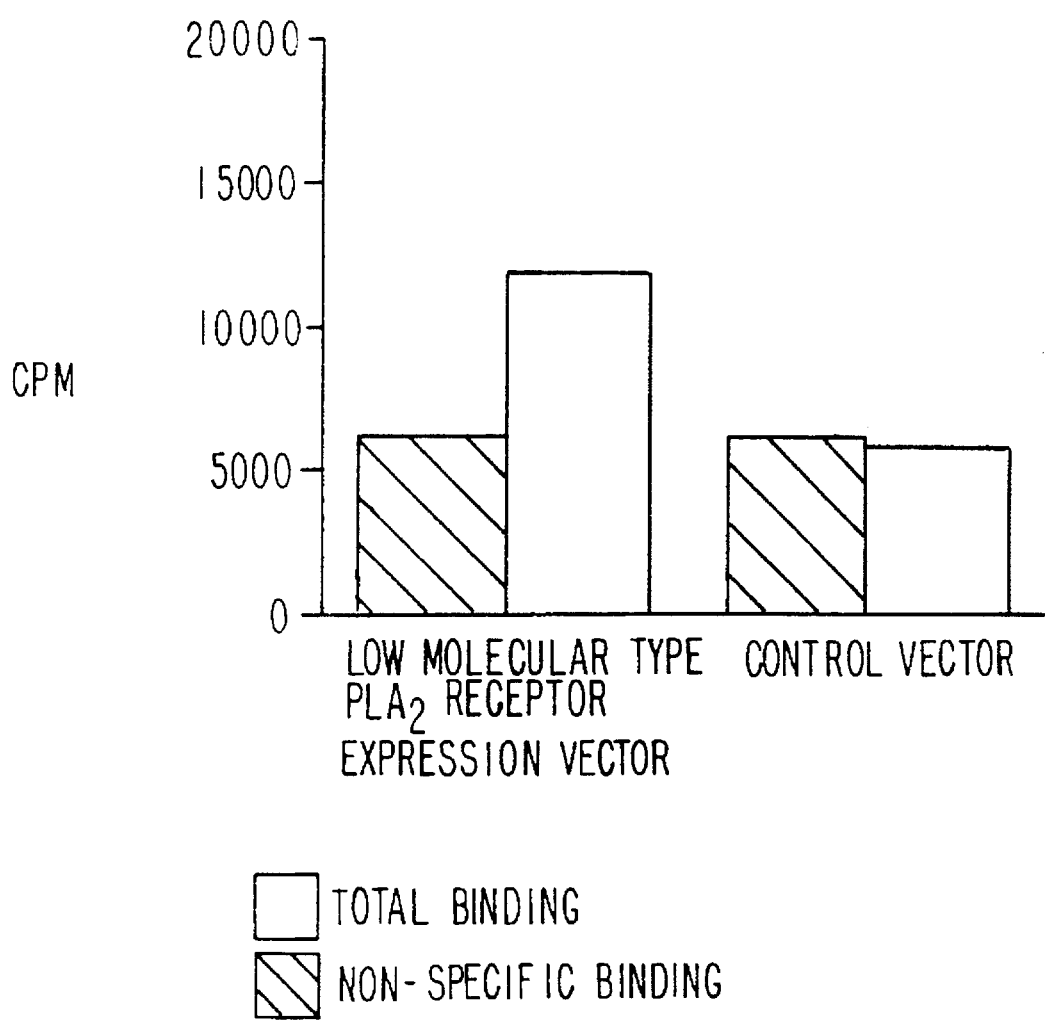
FIG. 6 shows the binding ability in a 200 μl medium three days after the transfection of COS cells with a low molecular weight type $PLA_2$-I receptor expression vector of the present invention and that with a control vector having no $PLA_2$-I receptor cDNA.

The low molecular weight type $PLA_2$-I receptor expression vector was introduced into COS7 cells in a similar manner as in Example 7, and the $PLA_2$-I binding ability in the supernatant was measured. The same procedure was repeated with regard to cells transfected with a control vector having no $PLA_2$-I receptor cDNA. The results are shown in FIG. 6. As in FIG. 5, the amount of non-specific binding is indicated with a mesh and that of total binding is indicated with dots. As is apparent from FIG. 6, the cells transfected with the low molecular weight type $PLA_2$-I receptor expression vector have a higher $PLA_2$-I binding ability as compared with those transfected with the control vector. This reveals that the $PLA_2$-I receptor binds to $PLA_2$-I through the domains CRD3 through CRD5 alone in the entire domain structure.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

The following specific sequence information and descriptions are provided in order to comply with the formal requirements of the submission of sequence data to the United States Patent and Trademark Office and are not intended to limit the scope of what the inventors regard as their invention. Variations in sequences which will become apparent to those skilled in the art upon review of this disclosure and which are encompassed by the attached claims are intended to be within the scope of the present invention. Further, it should be noted that efforts have been made to insure accuracy with respect to the specific sequences and characteristic description information describing such sequences, but some experimental error and/or deviation should be accounted for.

What is claimed is:

1. An isolated DNA molecule encoding a bovine group I phospholipase $A_2$ receptor comprising an amino acid sequence from Leu in the 486 position to Pro in the 940 position of SEQ ID NO: 11.

2. An isolated DNA molecule according to claim 1 comprising a base sequence from C in the 1795 position to C in the 3159 position of SEQ ID NO: 1.

3. An isolated DNA molecule according to claim 1 comprising a base sequence from G in the 340 position to A in the 4455 position of SEQ ID NO: 1.

4. An isolated DNA molecule according to claim 1 comprising a base sequence from A in the 280 position to A in the 4455 position of SEQ ID NO: 1.

5. An isolated DNA molecule according to claim 1 comprising a base sequence from G in the 340 position to G in the 4668 position of SEQ ID NO: 1.

6. An isolated DNA molecule according to claim 1 comprising a base sequence from A in the 280 position to G in the 4668 position of SEQ ID NO: 1.

7. An expression vector comprising the isolated DNA molecule of claim 1.

8. A host cell transformed with the expression vector of claim 7.

9. A host cell according to claim 8, wherein the host cell is a mammalian cell.

10. A method for producing a bovine group I phospholipase $A_2$ receptor comprising the steps of:

culturing the host cell of claim 8 in a medium under conditions suitable for production of the receptor; and recovering the produced bovine group I phospholipase $A_2$ receptor from the medium.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 4978
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: bovine ( i x ) FEATURE:
        ( A ) NAME/KEY: CDS
        ( B ) LOCATION: 280 to 4668
        ( C ) IDENTIFICATION METHOD: by similarity with known sequence
            or to an established consensus ( x i ) SEQUENCE DESCRIPTION: SEQ ID NO:1:

```
CCACCCCCTG  TTCCTCCTCC  TGCTCCAAGC  CGCAAAGGGA  GAACCTCCGC  GACTTTTCCG        60

TCTTCCAGCC  AGAGAGCCCC  CCCACCGTGG  CCACAGGGGT  GACTGACGAA  GTGGGTCTCG       120

GGGACGCAGG  GGTGGCGAGG  CCCCCGGGGA  GGGTTGGAGC  GCGGAGGAGG  CTGCGGTCCT       180

GCCCTCCGCC  ACCCCACCCA  CCGCAGGGCT  GGGCGCTGGG  CTTCGGCCCT  GGCCCCCCGC       240

GGGCGCTACA  CCGGGGACCG  GCGGGCCAAG  TGGTTAGCG  ATG  CCG  CTG  CTG  TCG         294
                                              Met  Pro  Leu  Leu  Ser
                                              -20

CTG  TCG  CTG  CTC  CTG  CTG  CTG  CTG  CAG  GTA  CCG  GCG  GGC  TCC  GCC  GAG   342
Leu  Ser  Leu  Leu  Leu  Leu  Leu  Leu  Gln  Val  Pro  Ala  Gly  Ser  Ala  Glu
-15                      -10                       -5                         1

ACC  GCG  GCG  TGG  GCA  GTC  ACC  CCC  GAG  CGG  CTC  CGC  GAG  TGG  CAA  GAT   390
Thr  Ala  Ala  Trp  Ala  Val  Thr  Pro  Glu  Arg  Leu  Arg  Glu  Trp  Gln  Asp
                5                       10                       15
```

| | | | | | | | | | | | | | | | | |
|---|---|---|---|---|---|---|---|---|---|---|---|---|---|---|---|---|
| AAA | GGA | ATC | TTC | ATT | ATC | CAA | AGT | GAG | AAC | CTC | GAG | AAA | TGT | ATT | CAA | 438 |
| Lys | Gly | Ile 20 | Phe | Ile | Ile | Gln | Ser 25 | Glu | Asn | Leu | Glu | Lys 30 | Cys | Ile | Gln | |
| GCC | AGC | AAA | TCT | ACA | CTG | ACC | CTG | GAG | AAC | TGC | AAA | CCA | CCC | AAC | AAG | 486 |
| Ala | Ser 35 | Lys | Ser | Thr | Leu | Thr 40 | Leu | Glu | Asn | Cys | Lys 45 | Pro | Pro | Asn | Lys | |
| TAC | ATG | CTG | TGG | AAG | TGG | GTT | TCA | AAC | CAC | CGC | TTA | TTT | AAC | ATC | GGA | 534 |
| Tyr 50 | Met | Leu | Trp | Lys | Trp 55 | Val | Ser | Asn | His | Arg 60 | Leu | Phe | Asn | Ile | Gly 65 | |
| GGC | AGT | GGC | TGC | CTG | GGC | CTG | AAC | GTG | TCT | AGT | CCA | GAG | CAG | CCA | CTG | 582 |
| Gly | Ser | Gly | Cys | Leu 70 | Gly | Leu | Asn | Val | Ser 75 | Ser | Pro | Glu | Gln | Pro 80 | Leu | |
| AGC | ATA | TAC | GAG | TGT | GAT | TCC | ACC | CAC | GTT | TCC | TTG | AAG | TGG | CAC | TGT | 630 |
| Ser | Ile | Tyr | Glu 85 | Cys | Asp | Ser | Thr | His 90 | Val | Ser | Leu | Lys | Trp 95 | His | Cys | |
| AAC | AAG | AAG | ACG | ATC | ACA | GGC | CCA | CTC | CAG | TAC | CTG | GTC | CAG | GTG | AAG | 678 |
| Asn | Lys | Lys 100 | Thr | Ile | Thr | Gly | Pro 105 | Leu | Gln | Tyr | Leu | Val 110 | Gln | Val | Lys | |
| CAG | GAC | AAC | ACG | CTT | GTG | GCC | TCA | AGG | AAA | TAT | CTC | CAT | AAG | TGG | GTT | 726 |
| Gln | Asp | Asn | Thr 115 | Leu | Val | Ala | Ser | Arg 120 | Lys | Tyr | Leu | His | Lys 125 | Trp | Val | |
| TCC | TAT | ATG | TCC | GGC | GGT | GGA | GGC | ATT | TGT | GAC | TAT | CTG | CAC | AAA | GAT | 774 |
| Ser 130 | Tyr | Met | Ser | Gly | Gly 135 | Gly | Gly | Ile | Cys | Asp 140 | Tyr | Leu | His | Lys | Asp 145 | |
| TTG | TAC | ACA | ATC | AAA | GGG | AAT | GCC | CAT | GGG | ACT | CCG | TGC | ATG | TTC | CCC | 822 |
| Leu | Tyr | Thr | Ile | Lys 150 | Gly | Asn | Ala | His | Gly 155 | Thr | Pro | Cys | Met | Phe 160 | Pro | |
| TTC | CAG | TAC | AAT | CAG | CAG | TGG | CAC | CAC | GAA | TGT | ACC | CGG | GAA | GGA | CGG | 870 |
| Phe | Gln | Tyr | Asn 165 | Gln | Gln | Trp | His | His 170 | Glu | Cys | Thr | Arg | Glu 175 | Gly | Arg | |
| GAA | GAC | AAC | TTG | CTG | TGG | TGT | GCC | ACT | ACC | AGC | CGA | TAC | GAA | AGA | GAC | 918 |
| Glu | Asp | Asn 180 | Leu | Leu | Trp | Cys | Ala 185 | Thr | Thr | Ser | Arg | Tyr 190 | Glu | Arg | Asp | |
| GAG | AAG | TGG | GGA | TTT | TGC | CCA | GAT | CCT | ACA | TCC | ACA | GAG | GTG | GGC | TGC | 966 |
| Glu | Lys | Trp 195 | Gly | Phe | Cys | Pro | Asp 200 | Pro | Thr | Ser | Thr | Glu 205 | Val | Gly | Cys | |
| GAT | GCA | GTC | TGG | GAG | AAG | GAT | CTC | CAT | TCA | CGC | ATT | TGC | TAC | CAA | TTC | 1014 |
| Asp 210 | Ala | Val | Trp | Glu | Lys 215 | Asp | Leu | His | Ser | Arg 220 | Ile | Cys | Tyr | Gln | Phe 225 | |
| AAT | CTG | CTT | TCC | TCC | CTG | TCC | TGG | AGT | GAG | GCT | CAT | TCT | TCA | TGC | CAG | 1062 |
| Asn | Leu | Leu | Ser | Ser 230 | Leu | Ser | Trp | Ser | Glu 235 | Ala | His | Ser | Ser | Cys 240 | Gln | |
| ATG | CAA | GGA | GCT | GCT | TTA | TTA | AGT | ATT | GCA | GAT | GAG | ACT | GAA | GAA | AAT | 1110 |
| Met | Gln | Gly | Ala 245 | Ala | Leu | Leu | Ser | Ile 250 | Ala | Asp | Glu | Thr | Glu 255 | Glu | Asn | |
| TTC | GTA | AGG | AAG | CAC | TTG | GGC | AGT | GAA | GCA | GTG | GAA | GTA | TGG | ATG | GGT | 1158 |
| Phe | Val | Arg 260 | Lys | His | Leu | Gly | Ser 265 | Glu | Ala | Val | Glu | Val 270 | Trp | Met | Gly | |
| CTG | AAT | CAG | CTG | GAT | GAA | GAT | GCT | GGT | TGG | CAG | TGG | TCT | GAT | AGA | ACA | 1206 |
| Leu | Asn 275 | Gln | Leu | Asp | Glu | Asp 280 | Ala | Gly | Trp | Gln | Trp 285 | Ser | Asp | Arg | Thr | |
| CCA | CTC | AAC | TAT | CTG | AAC | TGG | AAG | CCA | GAA | ATA | AAT | TTT | GAG | CCA | TTT | 1254 |
| Pro 290 | Leu | Asn | Tyr | Leu | Asn 295 | Trp | Lys | Pro | Glu | Ile 300 | Asn | Phe | Glu | Pro | Phe 305 | |
| GTT | GAA | TAT | CAC | TGT | GGA | ACA | TTT | AAT | GCA | TTT | ATG | CCA | AAG | GCC | TGG | 1302 |
| Val | Glu | Tyr | His | Cys 310 | Gly | Thr | Phe | Asn | Ala 315 | Phe | Met | Pro | Lys | Ala 320 | Trp | |
| AAA | AGT | CGG | GAT | TGT | GAG | TCT | ACC | TTG | CCC | TAC | GTG | TGT | AAA | AAA | TAT | 1350 |
| Lys | Ser | Arg | Asp 325 | Cys | Glu | Ser | Thr | Leu 330 | Pro | Tyr | Val | Cys | Lys 335 | Lys | Tyr | |

| | | | | | | | | | | | | | | | | |
|---|---|---|---|---|---|---|---|---|---|---|---|---|---|---|---|---|
| CTA | AAT | CCC | ACT | GAT | CAT | GGA | GTA | GTT | GAA | AAG | GAT | GCT | TGG | AAA | TAC | 1398 |
| Leu | Asn | Pro 340 | Thr | Asp | His | Gly | Val | Val 345 | Glu | Lys | Asp | Ala 350 | Trp | Lys | Tyr | |
| TAT | GCT | ACC | CAC | TGT | GAG | CCT | GGC | TGG | AAT | CCC | CAC | AAC | CGT | AAT | TGC | 1446 |
| Tyr | Ala | Thr 355 | His | Cys | Glu | Pro 360 | Gly | Trp | Asn | Pro | His 365 | Asn | Arg | Asn | Cys | |
| TAT | AAA | CTG | CAG | AAA | GAA | AAA | AAG | ACC | TGG | AAT | GAG | GCT | TTG | CAG | TCT | 1494 |
| Tyr 370 | Lys | Leu | Gln | Lys | Glu 375 | Lys | Lys | Thr | Trp | Asn 380 | Glu | Ala | Leu | Gln | Ser 385 | |
| TGC | CAG | TCC | AAC | AAC | AGT | GTA | TTA | ACA | GAC | ATC | ACT | TCG | TTA | GCA | GAG | 1542 |
| Cys | Gln | Ser | Asn | Asn 390 | Ser | Val | Leu | Thr | Asp 395 | Ile | Thr | Ser | Leu | Ala 400 | Glu | |
| GTG | GAG | TTT | CTT | GTA | ACC | CTC | CTT | GGA | GAT | GAA | AAT | GCA | TCA | GAA | ACA | 1590 |
| Val | Glu | Phe | Leu 405 | Val | Thr | Leu | Leu | Gly | Asp 410 | Glu | Asn | Ala | Ser 415 | Glu | Thr | |
| TGG | ATT | GGT | TTG | AGC | AGC | CAT | AAA | ATT | CCA | GTT | TCC | TTT | GAG | TGG | TCT | 1638 |
| Trp | Ile | Gly | Leu 420 | Ser | Ser | His | Lys | Ile 425 | Pro | Val | Ser | Phe | Glu 430 | Trp | Ser | |
| AAT | GGC | TCC | TCG | GTC | ACC | TTT | ACT | AAC | TGG | CAC | ACA | CTT | GAG | CCC | CAC | 1686 |
| Asn | Gly | Ser 435 | Ser | Val | Thr | Phe 440 | Thr | Asn | Trp | His | Thr 445 | Leu | Glu | Pro | His | |
| ATT | TTT | CCA | AAT | AGA | AGC | CAG | TTG | TGT | GTC | TCA | GCA | GAG | CAA | TCT | GAG | 1734 |
| Ile 450 | Phe | Pro | Asn | Arg | Ser 455 | Gln | Leu | Cys | Val | Ser 460 | Ala | Glu | Gln | Ser | Glu 465 | |
| GGA | CAC | TGG | AAA | GTT | AAA | AAT | TGC | GAA | GAA | ACA | CTT | TTT | TAC | CTT | TGT | 1782 |
| Gly | His | Trp | Lys | Val 470 | Lys | Asn | Cys | Glu | Glu 475 | Thr | Leu | Phe | Tyr | Leu 480 | Cys | |
| AAG | AAA | ACA | GGC | CTT | GTC | CTT | TCT | GAC | ACT | GAA | TCA | GGC | TGT | CAA | AAG | 1830 |
| Lys | Lys | Thr | Gly 485 | Leu | Val | Leu | Ser | Asp 490 | Thr | Glu | Ser | Gly | Cys 495 | Gln | Lys | |
| GGA | TGG | GAG | AGA | CAT | GGT | AAA | TTC | TGT | TAC | AAA | ATT | GAC | ACC | GTC | CTT | 1878 |
| Gly | Trp | Glu 500 | Arg | His | Gly | Lys | Phe 505 | Cys | Tyr | Lys | Ile | Asp 510 | Thr | Val | Leu | |
| CGA | AGC | TTT | GAC | CAT | GCC | TCC | AGT | GGT | TAC | TAC | TGT | CCT | CCT | GCG | CTT | 1926 |
| Arg | Ser | Phe 515 | Asp | His | Ala | Ser | Ser 520 | Gly | Tyr | Tyr | Cys | Pro 525 | Pro | Ala | Leu | |
| ATA | ACC | ATT | ACA | AGC | AGG | TTT | GAA | CAG | GCT | TTT | ATT | ACC | AGT | TTG | ATC | 1974 |
| Ile 530 | Thr | Ile | Thr | Ser | Arg 535 | Phe | Glu | Gln | Ala | Phe 540 | Ile | Thr | Ser | Leu | Ile 545 | |
| AGT | AGT | GTG | GTA | AAA | ACG | AAG | GAC | ACT | TAT | TTT | TGG | ATC | GCT | CTT | CAA | 2022 |
| Ser | Ser | Val | Val | Lys 550 | Thr | Lys | Asp | Thr | Tyr 555 | Phe | Trp | Ile | Ala | Leu 560 | Gln | |
| GAT | CAA | AAT | AAT | ACA | GGA | GAA | TAC | ACT | TGG | AAG | ACG | GCA | GGG | CAG | CAG | 2070 |
| Asp | Gln | Asn | Asn 565 | Thr | Gly | Glu | Tyr | Thr 570 | Trp | Lys | Thr | Ala | Gly 575 | Gln | Gln | |
| TTG | GAG | CCA | GTG | AAG | TAC | ACA | CAC | TGG | AAC | ACA | CGT | CAG | CCC | CGC | TAC | 2118 |
| Leu | Glu | Pro 580 | Val | Lys | Tyr | Thr | His 585 | Trp | Asn | Thr | Arg | Gln 590 | Pro | Arg | Tyr | |
| AGT | GGT | GGC | TGC | GTT | GTC | ATG | CGA | GGG | AGG | AGT | CAC | CCT | GGC | CGC | TGG | 2166 |
| Ser | Gly | Gly 595 | Cys | Val | Val | Met | Arg 600 | Gly | Arg | Ser | His | Pro 605 | Gly | Arg | Trp | |
| GAA | GTG | AGG | GAC | TGT | AGG | CAC | TTT | AAG | GCG | ATG | TCC | CTG | TGC | AAG | CAA | 2214 |
| Glu 610 | Val | Arg | Asp | Cys | Arg 615 | His | Phe | Lys | Ala | Met 620 | Ser | Leu | Cys | Lys | Gln 625 | |
| CCA | GTG | GAA | AAT | CGG | GAG | AAA | ACC | AAG | CAA | GAA | GAG | GGA | TGG | CCC | TTT | 2262 |
| Pro | Val | Glu | Asn | Arg 630 | Glu | Lys | Thr | Lys | Gln 635 | Glu | Glu | Gly | Trp | Pro 640 | Phe | |
| CAC | CCC | TGC | TAT | TTG | GAT | TGG | GAG | TCA | GAG | CCT | GGC | CTG | GCC | AGT | TGC | 2310 |
| His | Pro | Cys | Tyr 645 | Leu | Asp | Trp | Glu | Ser 650 | Glu | Pro | Gly | Leu | Ala 655 | Ser | Cys | |

| | | | | | | | | | | | | | | | | |
|---|---|---|---|---|---|---|---|---|---|---|---|---|---|---|---|---|
| TTC | AAG | GTA | TTT | CAT | AGT | GAA | AAA | GTC | CTG | ATG | AAA | AGA | ACA | TGG | AGA | 2358 |
| Phe | Lys | Val 660 | Phe | His | Ser | Glu | Lys 665 | Val | Leu | Met | Lys 670 | Arg | Thr | Trp | Arg | |
| CAA | GCT | GAA | GAA | TTT | TGT | GAA | GAA | TTT | GGA | GCT | CAT | CTT | GCA | AGC | TTT | 2406 |
| Gln | Ala 675 | Glu | Glu | Phe | Cys 680 | Glu | Glu | Phe | Gly | Ala 685 | His | Leu | Ala | Ser | Phe | |
| GCC | CAT | ATT | GAG | GAA | GAG | AAT | TTT | GTG | AAT | GAG | CTT | TTA | CAT | TCA | AAA | 2454 |
| Ala 690 | His | Ile | Glu | Glu 695 | Glu | Asn | Phe | Val | Asn 700 | Glu | Leu | Leu | His | Ser | Lys 705 | |
| TTT | AAT | CGG | ACA | GAA | GAA | AGG | CAG | TTC | TGG | ATT | GGA | TTT | AAT | AAA | AGA | 2502 |
| Phe | Asn | Arg | Thr | Glu 710 | Glu | Arg | Gln | Phe | Trp 715 | Ile | Gly | Phe | Asn | Lys 720 | Arg | |
| AAC | CCA | CTG | AAT | GCT | GGT | TCT | TGG | GAA | TGG | TCT | GAT | GGA | ACT | CCT | GTT | 2550 |
| Asn | Pro | Leu | Asn 725 | Ala | Gly | Ser | Trp | Glu 730 | Trp | Ser | Asp | Gly | Thr 735 | Pro | Val | |
| GTC | TCT | TCA | TTT | TTA | GAC | AAT | TCT | TAT | TTT | GGA | GAA | GAT | GCA | AGA | AAT | 2598 |
| Val | Ser | Ser 740 | Phe | Leu | Asp | Asn | Ser 745 | Tyr | Phe | Gly | Glu | Asp 750 | Ala | Arg | Asn | |
| TGT | GCT | GTT | TAT | AAG | GCA | AAT | AAA | ACG | TTG | CTA | CCC | TCA | TAC | TGT | GGT | 2646 |
| Cys | Ala | Val 755 | Tyr | Lys | Ala | Asn | Lys 760 | Thr | Leu | Leu | Pro 765 | Ser | Tyr | Cys | Gly | |
| TCC | AAA | CGT | GAA | TGG | ATA | TGC | AAA | ATT | CCA | AGA | GAT | GTG | AGA | CCC | AAG | 2694 |
| Ser 770 | Lys | Arg | Glu | Trp | Ile 775 | Cys | Lys | Ile | Pro | Arg 780 | Asp | Val | Arg | Pro | Lys 785 | |
| GTT | CCA | CCC | TGG | TAT | CAG | TAT | GAT | GCA | CCC | TGG | CTC | TTT | TAT | CAG | GAT | 2742 |
| Val | Pro | Pro | Trp | Tyr 790 | Gln | Tyr | Asp | Ala | Pro 795 | Trp | Leu | Phe | Tyr | Gln 800 | Asp | |
| GCA | GAG | TAC | CTT | TTT | CAT | ATT | TCT | GCC | TCA | GAA | TGG | TCC | TCC | TTT | GAG | 2790 |
| Ala | Glu | Tyr | Leu 805 | Phe | His | Ile | Ser | Ala 810 | Ser | Glu | Trp | Ser | Ser 815 | Phe | Glu | |
| TTT | GTC | TGT | GGC | TGG | CTG | CGC | AGT | GAT | ATT | CTC | ACT | ATT | CAT | TCT | GCA | 2838 |
| Phe | Val | Cys 820 | Gly | Trp | Leu | Arg | Ser 825 | Asp | Ile | Leu | Thr | Ile 830 | His | Ser | Ala | |
| CAC | GAA | CAA | GAA | TTC | ATC | CAC | AGC | AAA | ATA | AGA | GCG | CTA | TCA | AAG | TAT | 2886 |
| His | Glu 835 | Gln | Glu | Phe | Ile | His 840 | Ser | Lys | Ile | Arg | Ala 845 | Leu | Ser | Lys | Tyr | |
| GGT | GTA | AAT | TGG | TGG | ATT | GGA | CTT | CGA | GAA | GAA | AGA | GCC | AGT | GAT | GAA | 2934 |
| Gly 850 | Val | Asn | Trp | Trp | Ile 855 | Gly | Leu | Arg | Glu | Glu 860 | Arg | Ala | Ser | Asp | Glu 865 | |
| TTT | CGT | TGG | AGA | GAT | GGA | TCA | CCA | GTA | ATA | TAT | CAG | AAC | TGG | GAC | AAA | 2982 |
| Phe | Arg | Trp | Arg | Asp 870 | Gly | Ser | Pro | Val | Ile 875 | Tyr | Gln | Asn | Trp | Asp 880 | Lys | |
| GGA | AAA | GAA | AGA | TCT | ATG | GGC | CTT | AAT | GAG | AGC | CAG | AGG | TGT | GGC | TTC | 3030 |
| Gly | Lys | Glu | Arg 885 | Ser | Met | Gly | Leu | Asn 890 | Glu | Ser | Gln | Arg | Cys 895 | Gly | Phe | |
| ATT | TCA | TCC | ATA | ACA | GGT | CTC | TGG | GCG | AGT | GAA | GAG | TGT | TCA | ATT | TCT | 3078 |
| Ile | Ser | Ser 900 | Ile | Thr | Gly | Leu | Trp 905 | Ala | Ser | Glu | Glu | Cys 910 | Ser | Ile | Ser | |
| ATG | CCT | AGC | ATC | TGT | AAG | CGA | AAA | AAG | GTT | TGG | GTC | ATA | GAA | AAA | AAG | 3126 |
| Met | Pro 915 | Ser | Ile | Cys | Lys | Arg 920 | Lys | Lys | Val | Trp | Val 925 | Ile | Glu | Lys | Lys | |
| AAA | GAT | ATT | CCA | AAA | CAA | CAT | GGA | ACA | TGT | CCC | AAA | GGA | TGG | TTA | TAT | 3174 |
| Lys 930 | Asp | Ile | Pro | Lys | Gln 935 | His | Gly | Thr | Cys | Pro 940 | Lys | Gly | Trp | Leu | Tyr 945 | |
| TTT | GAC | TAT | AAG | TGC | CTT | TTG | CTG | AAA | ATC | CCT | GAA | GGC | CCA | AGT | GAC | 3222 |
| Phe | Asp | Tyr | Lys | Cys 950 | Leu | Leu | Leu | Lys | Ile 955 | Pro | Glu | Gly | Pro | Ser 960 | Asp | |
| TGG | AAG | AAC | TGG | ACA | TCT | GCT | CAA | GAT | TTT | TGT | GTT | GAA | GAA | GGG | GGG | 3270 |
| Trp | Lys | Asn | Trp 965 | Thr | Ser | Ala | Gln | Asp 970 | Phe | Cys | Val | Glu | Glu 975 | Gly | Gly | |

| | | | | | | | | | | | | | | | | |
|---|---|---|---|---|---|---|---|---|---|---|---|---|---|---|---|---|
| ACA | CTG | GTT | GCC | ATT | GAA | AAT | GAG | GTG | GAA | CAA | GCT | TTC | ATT | ACC | ATG | 3318 |
| Thr | Leu | Val | Ala | Ile | Glu | Asn | Glu | Val | Glu | Gln | Ala | Phe | Ile | Thr | Met | |
| | | 980 | | | | 985 | | | | | | 990 | | | | |
| AAT | CTT | TTT | GGC | CAT | ACC | ACT | AAT | GTG | TGG | ATA | GGG | TTA | CAA | GAT | GAT | 3366 |
| Asn | Leu | Phe | Gly | His | Thr | Thr | Asn | Val | Trp | Ile | Gly | Leu | Gln | Asp | Asp | |
| | 995 | | | | 1000 | | | | | | 1005 | | | | | |
| GAT | TAT | GAA | AAA | TGG | CTA | AAT | GGA | AGG | CCT | GTG | TCA | TAT | TCT | AAT | TGG | 3414 |
| Asp | Tyr | Glu | Lys | Trp | Leu | Asn | Gly | Arg | Pro | Val | Ser | Tyr | Ser | Asn | Trp | |
| 1010 | | | | | 1015 | | | | | 1020 | | | | | 1025 | |
| TCT | CCA | TTT | GAT | ACA | AAA | AAT | ATT | CCA | AAT | CAC | AAC | ACC | ACT | GAA | GTT | 3462 |
| Ser | Pro | Phe | Asp | Thr | Lys | Asn | Ile | Pro | Asn | His | Asn | Thr | Thr | Glu | Val | |
| | | | | 1030 | | | | | 1035 | | | | | 1040 | | |
| CAA | AAA | CGC | ATT | CCT | CTC | TGT | GGC | TTG | CTG | TCA | AAT | AAT | CCT | AAT | TTT | 3510 |
| Gln | Lys | Arg | Ile | Pro | Leu | Cys | Gly | Leu | Leu | Ser | Asn | Asn | Pro | Asn | Phe | |
| | | | 1045 | | | | | 1050 | | | | | 1055 | | | |
| CAT | TTC | ACT | GGA | AAA | TGG | TAT | TTT | GAA | GAC | TGT | AGA | GAA | GGT | TAT | GGG | 3558 |
| His | Phe | Thr | Gly | Lys | Trp | Tyr | Phe | Glu | Asp | Cys | Arg | Glu | Gly | Tyr | Gly | |
| | | 1060 | | | | | 1065 | | | | | 1070 | | | | |
| TTT | GTT | TGT | GAA | AAA | ATG | CAG | GAT | GCT | TCT | GGA | CAC | AGT | ATA | AAT | ACA | 3606 |
| Phe | Val | Cys | Glu | Lys | Met | Gln | Asp | Ala | Ser | Gly | His | Ser | Ile | Asn | Thr | |
| | 1075 | | | | | 1080 | | | | | 1085 | | | | | |
| TCT | GAT | ATG | TAT | CCA | ATC | CCT | AAT | ACC | TTA | GAA | TAT | GGA | AAC | AGA | ACT | 3654 |
| Ser | Asp | Met | Tyr | Pro | Ile | Pro | Asn | Thr | Leu | Glu | Tyr | Gly | Asn | Arg | Thr | |
| 1090 | | | | | 1095 | | | | | 1100 | | | | | 1105 | |
| TAC | AAA | ATA | ATT | AAT | GCA | AAT | ATG | ACT | TGG | TAT | ACA | GCA | CTA | AAA | ACC | 3702 |
| Tyr | Lys | Ile | Ile | Asn | Ala | Asn | Met | Thr | Trp | Tyr | Thr | Ala | Leu | Lys | Thr | |
| | | | | 1110 | | | | | 1115 | | | | | 1120 | | |
| TGC | CTG | ATG | CAT | GGA | GCA | GAA | CTG | GCC | AGC | ATT | ACA | GAC | CAG | TAC | CAC | 3750 |
| Cys | Leu | Met | His | Gly | Ala | Glu | Leu | Ala | Ser | Ile | Thr | Asp | Gln | Tyr | His | |
| | | | 1125 | | | | | 1130 | | | | | 1135 | | | |
| CAG | TCT | TTC | CTC | ACT | GTT | ATC | CTT | AAC | CGG | GTG | GGA | TAT | GCC | CAC | TGG | 3798 |
| Gln | Ser | Phe | Leu | Thr | Val | Ile | Leu | Asn | Arg | Val | Gly | Tyr | Ala | His | Trp | |
| | | | 1140 | | | | | 1145 | | | | | 1150 | | | |
| ATT | GGA | CTG | TTC | ACT | GAA | GAT | AAT | GGT | CTT | AGT | TTT | GAC | TGG | TCA | GAT | 3846 |
| Ile | Gly | Leu | Phe | Thr | Glu | Asp | Asn | Gly | Leu | Ser | Phe | Asp | Trp | Ser | Asp | |
| | | 1155 | | | | | 1160 | | | | | 1165 | | | | |
| GGC | ACC | AAA | TCC | TCC | TTC | ACT | TTT | TGG | AAA | GAT | GAT | GAA | TCA | TCC | TTC | 3894 |
| Gly | Thr | Lys | Ser | Ser | Phe | Thr | Phe | Trp | Lys | Asp | Asp | Glu | Ser | Ser | Phe | |
| 1170 | | | | | 1175 | | | | | 1180 | | | | | 1185 | |
| CTT | GGT | GAC | TGT | GTT | TTT | GCT | GAC | ACC | AGT | GGA | CGC | TGG | AGT | AGC | ACA | 3942 |
| Leu | Gly | Asp | Cys | Val | Phe | Ala | Asp | Thr | Ser | Gly | Arg | Trp | Ser | Ser | Thr | |
| | | | | 1190 | | | | | 1195 | | | | | 1200 | | |
| GCC | TGC | GAG | TCG | TAT | CTG | CAA | GGA | GCC | ATT | TGT | CAA | GTG | CCC | ACT | GAA | 3990 |
| Ala | Cys | Glu | Ser | Tyr | Leu | Gln | Gly | Ala | Ile | Cys | Gln | Val | Pro | Thr | Glu | |
| | | | | 1205 | | | | | 1210 | | | | | 1215 | | |
| ACA | AGA | CTG | TCT | GGA | CGC | CTA | GAG | TTG | TGC | TCA | GAA | ACA | TCA | ATT | CCC | 4038 |
| Thr | Arg | Leu | Ser | Gly | Arg | Leu | Glu | Leu | Cys | Ser | Glu | Thr | Ser | Ile | Pro | |
| | | | 1220 | | | | | 1225 | | | | | 1230 | | | |
| TGG | ATA | AAA | TTC | AAA | AGT | AAT | TGC | TAC | AGT | TTT | TCT | ACA | GTC | CTA | GAG | 4086 |
| Trp | Ile | Lys | Phe | Lys | Ser | Asn | Cys | Tyr | Ser | Phe | Ser | Thr | Val | Leu | Glu | |
| | 1235 | | | | | 1240 | | | | | 1245 | | | | | |
| AGT | ACA | AGT | TTT | GAG | GCT | GCT | CAT | GAA | TTT | TGC | AAA | AAG | AAA | GGC | TCT | 4134 |
| Ser | Thr | Ser | Phe | Glu | Ala | Ala | His | Glu | Phe | Cys | Lys | Lys | Lys | Gly | Ser | |
| 1250 | | | | | 1255 | | | | | 1260 | | | | | 1265 | |
| AAT | CTT | TTA | ACA | ATC | AAA | GAT | GAA | GCT | GAA | AAC | TCT | TTT | CTT | CTA | GAA | 4182 |
| Asn | Leu | Leu | Thr | Ile | Lys | Asp | Glu | Ala | Glu | Asn | Ser | Phe | Leu | Leu | Glu | |
| | | | | 1270 | | | | | 1275 | | | | | 1280 | | |
| GAG | CTT | TTA | GCT | TTC | CGT | TCT | TCA | GTC | CAG | ATG | ATT | TGG | CTG | AAT | GCT | 4230 |
| Glu | Leu | Leu | Ala | Phe | Arg | Ser | Ser | Val | Gln | Met | Ile | Trp | Leu | Asn | Ala | |
| | | | 1285 | | | | | 1290 | | | | | 1295 | | | |

| | | | | | | | | | | | | | | | | |
|---|---|---|---|---|---|---|---|---|---|---|---|---|---|---|---|---|
| CAG | TTT | GAT | GGT | GAC | AAT | GAA | ACC | ATA | AAG | TGG | TTT | GAT | GGA | ACT | CCC | 4278 |
| Gln | Phe | Asp | Gly | Asp | Asn | Glu | Thr | Ile | Lys | Trp | Phe | Asp | Gly | Thr | Pro | |
| | | 1300 | | | | | 1305 | | | | | 1310 | | | | |
| ACA | GAT | CAA | TCA | AAC | TGG | GGT | ATT | CGG | AAG | CCA | GAG | GTG | TAC | CAC | TTC | 4326 |
| Thr | Asp | Gln | Ser | Asn | Trp | Gly | Ile | Arg | Lys | Pro | Glu | Val | Tyr | His | Phe | |
| | | 1315 | | | | | 1320 | | | | | 1325 | | | | |
| AAA | CCC | CAT | CTG | TGT | GTT | GCC | CTG | AGG | ATT | CCT | GAA | GGA | GTG | TGG | CAA | 4374 |
| Lys | Pro | His | Leu | Cys | Val | Ala | Leu | Arg | Ile | Pro | Glu | Gly | Val | Trp | Gln | |
| 1330 | | | | | 1335 | | | | | 1340 | | | | | 1345 | |
| TTA | TCC | TCG | TGT | CAA | GAC | AAA | AAG | GGA | TTT | ATA | TGT | AAA | ATG | GAA | GCA | 4422 |
| Leu | Ser | Ser | Cys | Gln | Asp | Lys | Lys | Gly | Phe | Ile | Cys | Lys | Met | Glu | Ala | |
| | | | | 1350 | | | | | 1355 | | | | | 1360 | | |
| GAT | ATT | CAC | ACA | GTA | AAG | AAG | CAT | CCA | GGA | AAA | GGA | CCA | AGT | CAC | AGT | 4470 |
| Asp | Ile | His | Thr | Val | Lys | Lys | His | Pro | Gly | Lys | Gly | Pro | Ser | His | Ser | |
| | | | 1365 | | | | | 1370 | | | | | 1375 | | | |
| GTT | ATA | CCT | CTT | ACA | GTA | GCA | CTG | ACA | CTG | CTA | GTA | ATT | CTG | GCA | ATT | 4518 |
| Val | Ile | Pro | Leu | Thr | Val | Ala | Leu | Thr | Leu | Leu | Val | Ile | Leu | Ala | Ile | |
| | | | 1380 | | | | | 1385 | | | | | 1390 | | | |
| TCC | ACA | CTT | TCC | TTC | TGC | ATG | TAC | AAG | CAC | AGT | CAC | ATT | ATC | TTC | GGG | 4566 |
| Ser | Thr | Leu | Ser | Phe | Cys | Met | Tyr | Lys | His | Ser | His | Ile | Ile | Phe | Gly | |
| | | 1395 | | | | | 1400 | | | | | 1405 | | | | |
| AGA | CTT | GCT | CAG | TTT | AGA | AAT | CCT | TAC | TAT | CCT | TCA | GCC | AAC | TTT | AGT | 4614 |
| Arg | Leu | Ala | Gln | Phe | Arg | Asn | Pro | Tyr | Tyr | Pro | Ser | Ala | Asn | Phe | Ser | |
| 1410 | | | | | 1415 | | | | | 1420 | | | | | 1425 | |
| ACA | GTA | CAT | TTA | GAA | GAA | AAT | ATT | CTC | ATT | TCT | GAT | CTT | GAG | AAG | AAT | 4662 |
| Thr | Val | His | Leu | Glu | Glu | Asn | Ile | Leu | Ile | Ser | Asp | Leu | Glu | Lys | Asn | |
| | | | | 1430 | | | | | 1435 | | | | | 1440 | | |

| | | | | |
|---|---|---|---|---|
| GAC | CAG | TAATAACGAA | GTGAGAGAAC | ATCACGGCGG | TGAGAATGAG | 4708 |
| Asp | Gln | | | | | |

| | | | | |
|---|---|---|---|---|
| CAAAGAAGAG | TATTTTCCTT | TACAGCCAGA | TGCCACTATA | ATGTCAATTG | TGTTACCATC | 4768 |
| TTCGTTATTC | TTAAAATGAT | TACTGGTTTT | GAATTGTAAC | CAAATCAGAT | AGGTGTTCAT | 4828 |
| TTATTTATTT | CCTCAAACTG | TGATCTATTC | TTAAAAGGGG | GAAAATTTAC | AGTGCTTATT | 4888 |
| ATTCAGAAAA | CAAGAACTAT | TAAAAGCAAC | TCCCAAATGA | GACCCCTCAA | AAAAAAAAAA | 4948 |
| AAAAAAAAAA | AAAAAAAAA | AAAAAAAAA | | | | 4978 |

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 2:

GAGACCGCNG CNTGGGC                                                  17

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 3:

ACCGCNGCNT GGGCNGT                                                  17

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 4:

CTRTT Y R Y RT AGAAGTAGTT        20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 5:

GT Y CTRTT Y R Y RTAGAAGTA        20

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 6:

ACCGGCGGGC CAAGTGGTT        19

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 7:

CCACTCGCGG AGCCGCTCGG        20

( 2 ) INFORMATION FOR SEQ ID NO:8:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 8:

Glu Thr Ala Ala Trp Ala Val Thr Pro Glu Arg Leu Arg Glu Trp Gln
 1             5                10             15

Asp Lys Xaa Ile Phe Ile Lys
                20

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 9:

ACTGGCGGCC GCTCATTTTC CTGGATGCTT    30

( 2 ) INFORMATION FOR SEQ ID NO:10:

( i ) SEQUENCE CHARACTERISTICS:
        ( A ) LENGTH: 505 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 10:

Met Pro Leu Leu Ser Leu Ser Leu Leu Leu Leu Leu Gln Val Pro
 1               5                  10                  15

Ala Gly Ser Ala Glu Thr Ala Ala Trp Ala Val Thr Pro Glu Arg Leu
             20              25              30

Arg Glu Trp Gln Asp Lys Gly Ile Phe Ile Ile Gln Ser Glu Asn Leu
         35              40              45

Asp Leu Val Leu Ser Asp Thr Glu Ser Gly Cys Gln Lys Gly Trp Glu
     50              55              60

Arg His Gly Lys Phe Cys Tyr Lys Ile Asp Thr Val Leu Arg Ser Phe
65              70              75              80

Asp His Ala Ser Ser Gly Tyr Tyr Cys Pro Ala Leu Ile Thr Ile
                 85              90              95

Thr Ser Arg Phe Glu Gln Ala Phe Ile Thr Ser Leu Ile Ser Ser Val
             100             105             110

Val Lys Thr Lys Asp Thr Tyr Phe Trp Ile Ala Leu Gln Asp Gln Asn
         115             120             125

Asn Thr Gly Glu Tyr Thr Trp Lys Thr Ala Gly Gln Gln Leu Glu Pro
     130             135             140

Val Lys Tyr Thr His Trp Asn Thr Arg Gln Pro Arg Tyr Ser Gly Gly
145             150             155             160

Cys Val Val Met Arg Gly Arg Ser His Pro Gly Arg Trp Glu Val Arg
                 165             170             175

Asp Cys Arg His Phe Lys Ala Met Ser Leu Cys Lys Gln Pro Val Glu
             180             185             190

Asn Arg Glu Lys Thr Lys Gln Glu Glu Gly Trp Pro Phe His Pro Cys
         195             200             205

Tyr Leu Asp Trp Glu Ser Glu Pro Gly Leu Ala Ser Cys Phe Lys Val
     210             215             220

Phe His Ser Glu Lys Val Leu Met Lys Arg Thr Trp Arg Gln Ala Glu
225             230             235             240

Glu Phe Cys Glu Glu Phe Gly Ala His Leu Ala Ser Phe Ala His Ile
                 245             250             255

| Glu | Glu | Glu | Asn 260 | Phe | Val | Asn | Glu | Leu 265 | His | Ser | Lys | Phe 270 | Asn | Arg |
| Thr | Glu | Glu 275 | Arg | Gln | Phe | Trp | Ile 280 | Gly | Phe | Asn | Lys | Arg 285 | Asn | Pro | Leu |
| Asn | Ala 290 | Gly | Ser | Trp | Glu | Trp 295 | Ser | Asp | Gly | Thr | Pro 300 | Val | Val | Ser | Ser |
| Phe 305 | Leu | Asp | Asn | Ser | Tyr 310 | Phe | Gly | Glu | Asp | Arg 315 | Asn | Cys | Ala | Val 320 |
| Tyr | Lys | Ala | Asn | Lys 325 | Thr | Leu | Leu | Pro | Ser 330 | Tyr | Cys | Gly | Ser | Lys 335 | Arg |
| Glu | Trp | Ile | Cys 340 | Lys | Ile | Pro | Arg | Asp 345 | Val | Arg | Pro | Lys | Val 350 | Pro | Pro |
| Trp | Tyr | Gln 355 | Tyr | Asp | Ala | Pro | Trp 360 | Leu | Phe | Tyr | Gln | Asp 365 | Ala | Glu | Tyr |
| Leu | Phe 370 | His | Ile | Ser | Ala | Ser 375 | Glu | Trp | Ser | Ser | Phe 380 | Glu | Phe | Val | Cys |
| Gly 385 | Trp | Leu | Arg | Ser | Asp 390 | Ile | Leu | Thr | Ile | His 395 | Ser | Ala | His | Glu | Gln 400 |
| Glu | Phe | Ile | His | Ser 405 | Lys | Ile | Arg | Ala | Leu 410 | Ser | Lys | Tyr | Gly | Val 415 | Asn |
| Trp | Trp | Ile | Gly 420 | Leu | Arg | Glu | Glu | Arg 425 | Ala | Ser | Asp | Glu | Phe 430 | Arg | Trp |
| Arg | Asp | Gly 435 | Ser | Pro | Val | Ile | Tyr 440 | Gln | Asn | Trp | Asp | Lys 445 | Gly | Lys | Glu |
| Arg | Ser 450 | Met | Gly | Leu | Asn | Glu 455 | Ser | Gln | Arg | Cys | Gly 460 | Phe | Ile | Ser | Ser |
| Ile 465 | Thr | Gly | Leu | Trp | Ala 470 | Ser | Glu | Glu | Cys | Ser 475 | Ile | Ser | Met | Pro | Ser 480 |
| Ile | Cys | Lys | Arg | Lys 485 | Lys | Val | Trp | Val | Ile 490 | Glu | Lys | Lys | Lys | Asp 495 | Ile |
| Pro | Lys | Gln | His | Gly 500 | Thr | Cys | Pro | Asn 505 |

( 2 ) INFORMATION FOR SEQ ID NO:11:

( i ) SEQUENCE CHARACTERISTICS:
        ( A ) LENGTH: 1463
        ( B ) TYPE: amino acid
        ( C ) TOPOLOGY: linear ( i i ) MOLECULE TYPE: peptide ( x i ) SEQUENCE DESCRIPTION: SEQ ID NO:11:

| Met -20 | Pro | Leu | Leu | Ser | Leu -15 | Ser | Leu | Leu | Leu | Leu -10 | Leu | Leu | Gln | Val | Pro -5 |
| Ala | Gly | Ser | Ala | Glu 1 | Thr | Ala | Ala | Trp 5 | Ala | Val | Thr | Pro | Glu 10 | Arg | Leu |
| Arg | Glu | Trp 15 | Gln | Asp | Lys | Gly | Ile 20 | Phe | Ile | Ile | Gln | Ser 25 | Glu | Asn | Leu |
| Glu | Lys 30 | Cys | Ile | Gln | Ala | Ser 35 | Lys | Ser | Thr | Leu | Thr 40 | Leu | Glu | Asn | Cys |
| Lys 45 | Pro | Pro | Asn | Lys | Tyr 50 | Met | Leu | Trp | Lys | Trp 55 | Val | Ser | Asn | His | Arg 60 |
| Leu | Phe | Asn | Ile | Gly 65 | Gly | Ser | Gly | Cys | Leu 70 | Gly | Leu | Asn | Val | Ser 75 | Ser |
| Pro | Glu | Gln | Pro | Leu | Ser | Ile | Tyr | Glu | Cys | Asp | Ser | Thr | His | Val | Ser |

|   |   |   | 80 |   |   |   |   | 85 |   |   |   |   | 90 |   |   |
|---|---|---|---|---|---|---|---|---|---|---|---|---|---|---|---|
| Leu | Lys | Trp 95 | His | Cys | Asn | Lys | Lys 100 | Thr | Ile | Thr | Gly | Pro 105 | Leu | Gln | Tyr |
| Leu | Val 110 | Gln | Val | Lys | Gln | Asp 115 | Asn | Thr | Leu | Val | Ala 120 | Ser | Arg | Lys | Tyr |
| Leu 125 | His | Lys | Trp | Val | Ser 130 | Tyr | Met | Ser | Gly | Gly 135 | Gly | Gly | Ile | Cys | Asp 140 |
| Tyr | Leu | His | Lys | Asp 145 | Leu | Tyr | Thr | Ile | Lys 150 | Gly | Asn | Ala | His | Gly 155 | Thr |
| Pro | Cys | Met | Phe 160 | Pro | Phe | Gln | Tyr | Asn 165 | Gln | Gln | Trp | His | His 170 | Glu | Cys |
| Thr | Arg | Glu 175 | Gly | Arg | Glu | Asp | Asn 180 | Leu | Leu | Trp | Cys | Ala 185 | Thr | Thr | Ser |
| Arg | Tyr 190 | Glu | Arg | Asp | Glu | Lys 195 | Trp | Gly | Phe | Cys | Pro 200 | Asp | Pro | Thr | Ser |
| Thr 205 | Glu | Val | Gly | Cys | Asp 210 | Ala | Val | Trp | Glu | Lys 215 | Asp | Leu | His | Ser | Arg 220 |
| Ile | Cys | Tyr | Gln | Phe 225 | Asn | Leu | Leu | Ser | Ser 230 | Leu | Ser | Trp | Ser | Glu 235 | Ala |
| His | Ser | Ser | Cys 240 | Gln | Met | Gln | Gly | Ala 245 | Ala | Leu | Leu | Ser | Ile 250 | Ala | Asp |
| Glu | Thr | Glu 255 | Glu | Asn | Phe | Val | Arg 260 | Lys | His | Leu | Gly | Ser 265 | Glu | Ala | Val |
| Glu | Val 270 | Trp | Met | Gly | Leu | Asn 275 | Gln | Leu | Asp | Glu | Asp 280 | Ala | Gly | Trp | Gln |
| Trp 285 | Ser | Asp | Arg | Thr | Pro 290 | Leu | Asn | Tyr | Leu | Asn 295 | Trp | Lys | Pro | Glu | Ile 300 |
| Asn | Phe | Glu | Pro | Phe 305 | Val | Glu | Tyr | His | Cys 310 | Gly | Thr | Phe | Asn | Ala 315 | Phe |
| Met | Pro | Lys | Ala 320 | Trp | Lys | Ser | Arg | Asp 325 | Cys | Glu | Ser | Thr | Leu 330 | Pro | Tyr |
| Val | Cys | Lys 335 | Lys | Tyr | Leu | Asn | Pro 340 | Thr | Asp | His | Gly | Val 345 | Val | Glu | Lys |
| Asp | Ala 350 | Trp | Lys | Tyr | Tyr | Ala 355 | Thr | His | Cys | Glu | Pro 360 | Gly | Trp | Asn | Pro |
| His 365 | Asn | Arg | Asn | Cys | Tyr 370 | Lys | Leu | Gln | Lys | Glu 375 | Lys | Lys | Thr | Trp | Asn 380 |
| Glu | Ala | Leu | Gln | Ser 385 | Cys | Gln | Ser | Asn | Asn 390 | Ser | Val | Leu | Thr | Asp 395 | Ile |
| Thr | Ser | Leu | Ala 400 | Glu | Val | Glu | Phe | Leu 405 | Val | Thr | Leu | Leu | Gly 410 | Asp | Glu |
| Asn | Ala | Ser 415 | Glu | Thr | Trp | Ile | Gly 420 | Leu | Ser | Ser | His | Lys 425 | Ile | Pro | Val |
| Ser | Phe 430 | Glu | Trp | Ser | Asn | Gly 435 | Ser | Ser | Val | Thr | Phe 440 | Thr | Asn | Trp | His |
| Thr 445 | Leu | Glu | Pro | His | Ile 450 | Phe | Pro | Asn | Arg | Ser 455 | Gln | Leu | Cys | Val | Ser 460 |
| Ala | Glu | Gln | Ser | Glu 465 | Gly | His | Trp | Lys | Val 470 | Lys | Asn | Cys | Glu | Glu 475 | Thr |
| Leu | Phe | Tyr | Leu 480 | Cys | Lys | Lys | Thr | Gly 485 | Leu | Val | Leu | Ser | Asp 490 | Thr | Glu |
| Ser | Gly | Cys 495 | Gln | Lys | Gly | Trp | Glu 500 | Arg | His | Gly | Lys | Phe 505 | Cys | Tyr | Lys |

```
Ile Asp Thr Val Leu Arg Ser Phe Asp His Ala Ser Ser Gly Tyr Tyr
    510                 515                 520

Cys Pro Pro Ala Leu Ile Thr Ile Thr Ser Arg Phe Glu Gln Ala Phe
525                 530                 535                 540

Ile Thr Ser Leu Ile Ser Ser Val Val Lys Thr Lys Asp Thr Tyr Phe
                545                 550                 555

Trp Ile Ala Leu Gln Asp Gln Asn Asn Thr Gly Glu Tyr Thr Trp Lys
                560                 565                 570

Thr Ala Gly Gln Gln Leu Glu Pro Val Lys Tyr Thr His Trp Asn Thr
        575                 580                 585

Arg Gln Pro Arg Tyr Ser Gly Gly Cys Val Val Met Arg Gly Arg Ser
        590                 595                 600

His Pro Gly Arg Trp Glu Val Arg Asp Cys Arg His Phe Lys Ala Met
605                 610                 615                 620

Ser Leu Cys Lys Gln Pro Val Glu Asn Arg Glu Lys Thr Lys Gln Glu
                625                 630                 635

Glu Gly Trp Pro Phe His Pro Cys Tyr Leu Asp Trp Glu Ser Glu Pro
            640                 645                 650

Gly Leu Ala Ser Cys Phe Lys Val Phe His Ser Glu Lys Val Leu Met
        655                 660                 665

Lys Arg Thr Trp Arg Gln Ala Glu Glu Phe Cys Glu Glu Phe Gly Ala
    670                 675                 680

His Leu Ala Ser Phe Ala His Ile Glu Glu Glu Asn Phe Val Asn Glu
685                 690                 695                 700

Leu Leu His Ser Lys Phe Asn Arg Thr Glu Arg Gln Phe Trp Ile
                705                 710                 715

Gly Phe Asn Lys Arg Asn Pro Leu Asn Ala Gly Ser Trp Glu Trp Ser
            720                 725                 730

Asp Gly Thr Pro Val Val Ser Ser Phe Leu Asp Asn Ser Tyr Phe Gly
        735                 740                 745

Glu Asp Ala Arg Asn Cys Ala Val Tyr Lys Ala Asn Lys Thr Leu Leu
    750                 755                 760

Pro Ser Tyr Cys Gly Ser Lys Arg Glu Trp Ile Cys Lys Ile Pro Arg
765                 770                 775                 780

Asp Val Arg Pro Lys Val Pro Pro Trp Tyr Gln Tyr Asp Ala Pro Trp
            785                 790                 795

Leu Phe Tyr Gln Asp Ala Glu Tyr Leu Phe His Ile Ser Ala Ser Glu
            800                 805                 810

Trp Ser Ser Phe Glu Phe Val Cys Gly Trp Leu Arg Ser Asp Ile Leu
    815                 820                 825

Thr Ile His Ser Ala His Glu Gln Glu Phe Ile His Ser Lys Ile Arg
        830                 835                 840

Ala Leu Ser Lys Tyr Gly Val Asn Trp Trp Ile Gly Leu Arg Glu Glu
845                 850                 855                 860

Arg Ala Ser Asp Glu Phe Arg Trp Arg Asp Gly Ser Pro Val Ile Tyr
            865                 870                 875

Gln Asn Trp Asp Lys Gly Lys Glu Arg Ser Met Gly Leu Asn Glu Ser
            880                 885                 890

Gln Arg Cys Gly Phe Ile Ser Ser Ile Thr Gly Leu Trp Ala Ser Glu
        895                 900                 905

Glu Cys Ser Ile Ser Met Pro Ser Ile Cys Lys Arg Lys Lys Val Trp
    910                 915                 920

Val Ile Glu Lys Lys Lys Asp Ile Pro Lys Gln His Gly Thr Cys Pro
925                 930                 935                 940
```

```
Lys Gly Trp Leu Tyr Phe Asp Tyr Lys Cys Leu Leu Leu Lys Ile Pro
                945                 950                 955
Glu Gly Pro Ser Asp Trp Lys Asn Trp Thr Ser Ala Gln Asp Phe Cys
            960                 965                 970
Val Glu Gly Gly Thr Leu Val Ala Ile Glu Asn Glu Val Glu Gln
    975                 980                 985
Ala Phe Ile Thr Met Asn Leu Phe Gly His Thr Thr Asn Val Trp Ile
        990                 995                 1000
Gly Leu Gln Asp Asp Asp Tyr Glu Lys Trp Leu Asn Gly Arg Pro Val
1005                1010                1015                1020
Ser Tyr Ser Asn Trp Ser Pro Phe Asp Thr Lys Asn Ile Pro Asn His
            1025                1030                1035
Asn Thr Thr Glu Val Gln Lys Arg Ile Pro Leu Cys Gly Leu Leu Ser
                1040                1045                1050
Asn Asn Pro Asn Phe His Phe Thr Gly Lys Trp Tyr Phe Glu Asp Cys
            1055                1060                1065
Arg Glu Gly Tyr Gly Phe Val Cys Glu Lys Met Gln Asp Ala Ser Gly
            1070                1075                1080
His Ser Ile Asn Thr Ser Asp Met Tyr Pro Ile Pro Asn Thr Leu Glu
1085                1090                1095                1100
Tyr Gly Asn Arg Thr Tyr Lys Ile Ile Asn Ala Asn Met Thr Trp Tyr
                1105                1110                1115
Thr Ala Leu Lys Thr Cys Leu Met His Gly Ala Glu Leu Ala Ser Ile
            1120                1125                1130
Thr Asp Gln Tyr His Gln Ser Phe Leu Thr Val Ile Leu Asn Arg Val
             1135                1140                1145
Gly Tyr Ala His Trp Ile Gly Leu Phe Thr Glu Asp Asn Gly Leu Ser
1150                1155                1160
Phe Asp Trp Ser Asp Gly Thr Lys Ser Ser Phe Thr Phe Trp Lys Asp
1165                1170                1175                1180
Asp Glu Ser Ser Phe Leu Gly Asp Cys Val Phe Ala Asp Thr Ser Gly
            1185                1190                1195
Arg Trp Ser Ser Thr Ala Cys Glu Ser Tyr Leu Gln Gly Ala Ile Cys
            1200                1205                1210
Gln Val Pro Thr Glu Thr Arg Leu Ser Gly Arg Leu Glu Leu Cys Ser
            1215                1220                1225
Glu Thr Ser Ile Pro Trp Ile Lys Phe Lys Ser Asn Cys Tyr Ser Phe
            1230                1235                1240
Ser Thr Val Leu Glu Ser Thr Ser Phe Glu Ala Ala His Glu Phe Cys
1245                1250                1255                1260
Lys Lys Lys Gly Ser Asn Leu Leu Thr Ile Lys Asp Glu Ala Glu Asn
                1265                1270                1275
Ser Phe Leu Leu Glu Glu Leu Leu Ala Phe Arg Ser Ser Val Gln Met
            1280                1285                1290
Ile Trp Leu Asn Ala Gln Phe Asp Gly Asp Asn Glu Thr Ile Lys Trp
            1295                1300                1305
Phe Asp Gly Thr Pro Thr Asp Gln Ser Asn Trp Gly Ile Arg Lys Pro
    1310                1315                1320
Glu Val Tyr His Phe Lys Pro His Leu Cys Val Ala Leu Arg Ile Pro
1325                1330                1335                1340
Glu Gly Val Trp Gln Leu Ser Ser Cys Gln Asp Lys Lys Gly Phe Ile
                1345                1350                1355
Cys Lys Met Glu Ala Asp Ile His Thr Val Lys Lys His Pro Gly Lys
```

|   | 1360 |   |   |   |   | 1365 |   |   |   |   | 1370 |   |   |
|---|---|---|---|---|---|---|---|---|---|---|---|---|---|
| Gly | Pro | Ser | His | Ser | Val | Ile | Pro | Leu | Thr | Val | Ala | Leu | Thr | Leu | Leu |
|   |   | 1375 |   |   |   |   | 1380 |   |   |   |   | 1385 |   |   |
| Val | Ile | Leu | Ala | Ile | Ser | Thr | Leu | Ser | Phe | Cys | Met | Tyr | Lys | His | Ser |
|   | 1390 |   |   |   |   | 1395 |   |   |   |   | 1400 |   |   |   |   |
| His | Ile | Ile | Phe | Gly | Arg | Leu | Ala | Gln | Phe | Arg | Asn | Pro | Tyr | Tyr | Pro |
| 1405 |   |   |   |   | 1410 |   |   |   |   | 1415 |   |   |   |   | 1420 |
| Ser | Ala | Asn | Phe | Ser | Thr | Val | His | Leu | Glu | Glu | Asn | Ile | Leu | Ile | Ser |
|   |   |   |   | 1425 |   |   |   |   | 1430 |   |   |   |   | 1435 |   |
| Asp | Leu | Glu | Lys | Asn | Asp | Gln |   |   |   |   |   |   |   |   |   |
|   |   |   |   | 1440 |   |   |   |   |   |   |   |   |   |   |   |